United States Patent [19]
Folkman et al.

[11] Patent Number: 5,886,141
[45] Date of Patent: Mar. 23, 1999

[54] SMOOTH MUSCLE MITOGEN PEPTIDES AND DNA CODING THEREFOR

[75] Inventors: Moses J. Folkman, Brookline; Yuen Shing, Randolph, both of Mass.; Koichi Igarashi, Kyoto, Japan

[73] Assignees: Takeda Chemical Industries, Ltd., Osaka, Japan; Children's Medical Center Corporation, Boston, Mass.

[21] Appl. No.: 465,794

[22] Filed: Jun. 6, 1995

Related U.S. Application Data

[63] Continuation of Ser. No. 7,126, Jan. 21, 1993, abandoned, which is a continuation-in-part of Ser. No. 994,776, Dec. 22, 1992, abandoned, Ser. No. 872,597, Apr. 23, 1992, abandoned, and Ser. No. 872,792, Apr. 23, 1992, abandoned, said Ser. No. 994,776, Ser. No. 872,597, and Ser. No. 872,792, each is a continuation-in-part of Ser. No.833,552, Feb. 10, 1992, abandoned, and Ser. No. 832,939, Feb. 10, 1992, abandoned, each is a continuation-in-part of Ser. No.766,354, Sep. 26, 1991, abandoned, which is a continuation-in-part of Ser. No. 604,778, Oct. 26, 1990, Pat. No. 5,229,493.

[51] Int. Cl.$^6$ .............................. C07K 14/00; C07K 7/06; C07K 7/08

[52] U.S. Cl. .................... 530/300; 530/399; 530/350; 530/329; 530/327; 435/69.1

[58] Field of Search ................................... 530/350, 300, 530/329, 327, 399; 435/69.1

[56] References Cited

U.S. PATENT DOCUMENTS

| | | | |
|---|---|---|---|
| 5,229,493 | 7/1993 | Folkman et al. | 530/350 |
| 5,328,986 | 7/1994 | Folkman | 530/350 |

FOREIGN PATENT DOCUMENTS

| | | |
|---|---|---|
| 0177957 | 10/1985 | European Pat. Off. . |
| 0482623A2 | 10/1991 | European Pat. Off. . |

OTHER PUBLICATIONS

American Type Culture Collection Catalogue of Cell Lines & Hybridoma, p. 161, ATCC CRL1682+1687, 1992.
Tarentino et al., J. Biol. Chem., 249, 818–824, 1974.
Wallace et al., Methods in Enzymology, v152, p. 432, Academic Press, 1987.
Schwartz, et al., Circulation Research, 58(4) :427 (1986).
Ross and Glomset, N. Engl. J. Med., 295:369–377 & 420–425 (1976).
Oka & Orth, J. Clin. Inves., 72:249–259 (1983).
Tucker, et al., Science, 266:705–777 (1984).
Kohler, et al, Nature, 256:495 (1975).
Huse, et al., Science, 246:1275 (1989).
Shing, et al., Methods in Enzymology, 146B:42–48 (1987).
Yung–Chih Wang et al., J. of Cell Biology, 106(3):797–803 (1988).
Shing, et al,. J. of Cell Biology, 111(5), part 2 p. 227a, abstract No. 1266 (1990).

*Primary Examiner*—Sally P. Teng
*Attorney, Agent, or Firm*—David G. Conlin; David S. Resnick; Dike, Bronstein, Roberts & Cushman, LLP

[57] ABSTRACT

A recombinant non-glycosylated mammalian growth factor (BTC-GF) stimulates proliferation of human smooth muscle cells. Especially, the amino acid sequence of the protein deduced from the nucleotide sequence coding for human BTC-GF is as that comprising the amino acids No. 1 to No. 147 of FIG. 10 (SEQ ID NO:5) or the amino acids No. 1 to 80 of FIG. 10 (SEQ ID NO:18), and the amino acid sequence of the protein deduced from the nucleotide sequence coding for mouse BTC-GF is as that comprising the amino acids No. 1 to No. 146 of FIG. 9 (SEQ ID NO:17).

5 Claims, 22 Drawing Sheets

1  2  3  4  5  6  7  8  9  10 11 12 13 14 15 16 17 18 19 20 21 22 23 24
Asp-Gly-(7)-Thr-(7)-Arg-Thr-Pro-Glu-(7)-Asn-Gly-(S)-Leu-(7)-(7)-(A)-(P)-( )-( )-( )-( )-( )-( )

Asp-Gly-(7)-Thr-(7)-Arg-Thr-Pro-Glu-Thr-Asn-Gly-Ser-Leu-(7)-Gly-Ala-Pro0(G)-Glu-Glu-(R)-Thr-(R)

aa    = High Confidence

[aa]  = Probable/Reasonable (aa)  = Possible/Low Confidence

[7]   = Unidentifiable

FIG. 7

(aa)ₐ - Thr His Phe Ser Arg Cys Pro Lys Gln Tyr L??

His Tyr Cys Ile His Gly Arg Cys Arg Phe Val Val Asp

Glu Gln Thr Pro Ser Cys Ile Cys Glu Lys Gly Tyr Phe

Gly Ala Arg Cys Glu Arg Val Asp Leu Phe Tyr - (aa)ₐ

```
GAATTCGCGG CCGCGTTTTC AAGCACCCTC TCGGTGCCAG GGCCCAGGAA GGGCATAGAG    60

AAGGAACCTG AGGACTCATC CAGGGGCTGC CCTGCCCCTC ACAGCACAGT TG ATG       115
                                                          Met
                                                          -31
GAC CCA ACA GCC CCG GGT AGC AGT GTC AGC TCC CTG CCG CTG CTC CTG    163
Asp Pro Thr Ala Pro Gly Ser Ser Val Ser Ser Leu Pro Leu Leu Leu
-30             -25                 -20                 -15
GTC CTT GCC CTG GGT CTT GCA ATT CTC CAC TGT GTG GTA GCA GAT GGG    211
Val Leu Ala Leu Gly Leu Ala Ile Leu His Cys Val Val Ala Asp Gly
                -10             -5                      1
AAC ACA ACC AGA ACA CCA GAA ACC AAT GGC TCT CTT TGT GGA GCT CCT    259
Asn Thr Thr Arg Thr Pro Glu Thr Asn Gly Ser Leu Cys Gly Ala Pro
            5                   10                  15
GGG GAA AAC TGC ACA GGT ACC ACC CCT AGA CAG AAA GTG AAA ACC CAC    307
Gly Glu Asn Cys Thr Gly Thr Thr Pro Arg Gln Lys Val Lys Thr His
        20                  25                  30
TTC TCT CGG TGC CCC AAG CAG TAC AAG CAT TAC TGC ATC CAT GGG AGA    355
Phe Ser Arg Cys Pro Lys Gln Tyr Lys His Tyr Cys Ile His Gly Arg
35                  40                  45                  50
TGC CGC TTC GTG GTG GAC GAG CAA ACT CCC TCC TGC ATC TGT GAG AAA    403
Cys Arg Phe Val Val Asp Glu Gln Thr Pro Ser Cys Ile Cys Glu Lys
                55                  60                  65
GGC TAC TTT GGG GCT CGG TGT GAG CGA GTG GAC CTG TTT TAC CTC CAG    451
Gly Tyr Phe Gly Ala Arg Cys Glu Arg Val Asp Leu Phe Tyr Leu Gln
            70                  75                  80
CAG GAC CGG GGG CAG ATC CTG GTG GTC TGC TTG ATA GTG GTC ATG GTG    499
Gln Asp Arg Gly Gln Ile Leu Val Val Cys Leu Ile Val Val Met Val
        85                  90                  95
GTG TTC ATC ATT TTA GTC ATC GGC GTC TGC ACC TGC TGT CAT CCT CTT    547
Val Phe Ile Ile Leu Val Ile Gly Val Cys Thr Cys Cys His Pro Leu
    100                 105                 110
CGG AAA CAT CGT AAA AAA AAG AAG GAA GAG AAA ATG GAG ACT TTG GAT    595
Arg Lys His Arg Lys Lys Lys Lys Glu Glu Lys Met Glu Thr Leu Asp
115                 120                 125                 130
AAA GAT AAA ACT CCC ATA AGT GAA GAT ATT CAA GAG ACC AAT ATT GCT    643
Lys Asp Lys Thr Pro Ile Ser Glu Asp Ile Gln Glu Thr Asn Ile Ala
            135                 140                 145
TAACGGTTAT AAAGTTATCA CAAGCTGGTG GCAAGCTACA AAAGACCTGA CTCATTCCCA    703
GATGGACAGG ACATGTCTCA GGAAAACAGC TAGCAGAAAT GAATGTTTAA ATATTGTATT    763
TACTTTTTTT ATTTGTAACT GTGTGTTGCT TGTTATTGTT TTTAATAACG ATATATTTTT    823
TTTGTTACAG CCTAGTAGTT GAGAAAAAAT AACCTGGTTA GGTGATGACA AAAATAAGGG    883
ACATTTGAAT ATAAACTTTG TTGCCAGGAT TATTAAATAA ATAAAAGAAA AGTGGAAAAG    943
AAGTTAGATT TTTAAGAACT AATTCACCAC CACGCAATGG TAGTACATGC CTTTAATCCC   1003
AGGACTTGGG AGGCAGAGGC AGGCAAATCT CTGTGAGTTC AAGGCCAGCC TGGTCTACAA   1063
AGAAAGTTCC AAAATAGCCA AGACTACAAC AGAGGAACAC TGTCTCAAAA AACCTAACCA   1123
ACCAACCAAC CAAACAAGCA AGCAAAACCC TGTCAATAAT AGGCGGCCGC GAATTC       1179
```

FIG. 10

```
CAGCGTGGAG GCTCCAAGGA CCAAGTCCTG CGCCTCTTTG GCGGGGTGTG TGCAGGAGGA        60
GGGGGGATAA ATAGGAGGCT CCCTCCTCCC GGCGACATTC ACGGAGCCGG CCGGCCTCCC       120
GCCCTGGGTG TTTCCCTGCC TTGTAGCCAG GGTGCCAGCC TGGGAAGTAG TTTCGTTTCC       180
TTCTGCCTCC GGGATTAGTT TCCAGGCACC CTCTCAGGCG CCCGAGGCCC GGGAAGGGGG       240
CGAAGAAGGA GGGAGACTTG TCTAGGGGCT GCCCGGCCCG GCAGAGCGGG GTTG ATG        297
                                                             Met
                                                             -31
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| GAC | CGG | GCC | GCC | CGG | TGC | AGC | GGC | GCC | AGC | TCC | CTG | CCA | CTG | CTC | CTG | 345 |
| Asp | Arg | Ala | Ala | Arg | Cys | Ser | Gly | Ala | Ser | Ser | Leu | Pro | Leu | Leu | Leu |     |
| -30 |     |     |     | -25 |     |     |     |     | -20 |     |     |     |     | -15 |     |     |
| GCC | CTT | GCC | CTG | GGT | CTA | GTG | ATC | CTT | CAC | TGT | GTG | GTG | GCA | GAT | GGG | 393 |
| Ala | Leu | Ala | Leu | Gly | Leu | Val | Ile | Leu | His | Cys | Val | Val | Ala | Asp | Gly |     |
|     |     |     | -10 |     |     |     |     | -5  |     |     |     |     |     | 1   |     |     |
| AAT | TCC | ACC | AGA | AGT | CCT | GAA | ACT | AAT | GGC | CTC | CTC | TGT | GGA | GAC | CCT | 441 |
| Asn | Ser | Thr | Arg | Ser | Pro | Glu | Thr | Asn | Gly | Leu | Leu | Cys | Gly | Asp | Pro |     |
|     |     | 5   |     |     |     |     | 10  |     |     |     |     | 15  |     |     |     |     |
| GAG | GAA | AAC | TGT | GCA | GCT | ACC | ACC | ACA | CAA | TCA | AAG | CGG | AAA | GGC | CAC | 489 |
| Glu | Glu | Asn | Cys | Ala | Ala | Thr | Thr | Thr | Gln | Ser | Lys | Arg | Lys | Gly | His |     |
|     | 20  |     |     |     |     | 25  |     |     |     |     | 30  |     |     |     |     |     |
| TTC | TCT | AGG | TGC | CCC | AAG | CAA | TAC | AAG | CAT | TAC | TGC | ATC | AAA | GGG | AGA | 537 |
| Phe | Ser | Arg | Cys | Pro | Lys | Gln | Tyr | Lys | His | Tyr | Cys | Ile | Lys | Gly | Arg |     |
| 35  |     |     |     |     | 40  |     |     |     |     | 45  |     |     |     |     | 50  |     |
| TGC | CGC | TTC | GTG | GTG | GCC | GAG | CAG | ACG | CCC | TCC | TGT | GTC | TGT | GAT | GAA | 585 |
| Cys | Arg | Phe | Val | Val | Ala | Glu | Gln | Thr | Pro | Ser | Cys | Val | Cys | Asp | Glu |     |
|     |     |     | 55  |     |     |     |     | 60  |     |     |     |     | 65  |     |     |     |
| GGC | TAC | ATT | GGA | GCA | AGG | TGT | GAG | AGA | GTT | GAC | TTG | TTT | TAC | CTA | AGA | 633 |
| Gly | Tyr | Ile | Gly | Ala | Arg | Cys | Glu | Arg | Val | Asp | Leu | Phe | Tyr | Leu | Arg |     |
|     |     | 70  |     |     |     |     | 75  |     |     |     |     | 80  |     |     |     |     |
| GGA | GAC | AGA | GGA | CAG | ATT | CTG | GTG | ATT | TGT | TTG | ATA | GCA | GTT | ATG | GTA | 681 |
| Gly | Asp | Arg | Gly | Gln | Ile | Leu | Val | Ile | Cys | Leu | Ile | Ala | Val | Met | Val |     |
|     | 85  |     |     |     |     | 90  |     |     |     |     | 95  |     |     |     |     |     |
| GTT | TTT | ATT | ATT | TTG | GTC | ATC | GGT | GTC | TGC | ACA | TGC | TGT | CAC | CCT | CTT | 729 |
| Val | Phe | Ile | Ile | Leu | Val | Ile | Gly | Val | Cys | Thr | Cys | Cys | His | Pro | Leu |     |
|     | 100 |     |     |     |     | 105 |     |     |     |     | 110 |     |     |     |     |     |
| CGG | AAA | CGT | CGT | AAA | AGA | AAG | AAG | AAA | GAA | GAA | GAA | ATG | GAA | ACT | CTG | 777 |
| Arg | Lys | Arg | Arg | Lys | Arg | Lys | Lys | Lys | Glu | Glu | Glu | Met | Glu | Thr | Leu |     |
| 115 |     |     |     | 120 |     |     |     |     | 125 |     |     |     |     | 130 |     |     |
| GGT | AAA | GAT | ATA | ACT | CCT | ATC | AAT | GAA | GAT | ATT | GAA | GAG | ACA | AAT | ATT | 825 |
| Gly | Lys | Asp | Ile | Thr | Pro | Ile | Asn | Glu | Asp | Ile | Glu | Glu | Thr | Asn | Ile |     |
|     |     |     | 135 |     |     |     |     | 140 |     |     |     |     | 145 |     |     |     |

```
GCT T AAAAGGCTAT GAAGTTACCT CCAGGTTGGT GGCAAGCTGC AAAGTGCCTT         879
Ala
GCTCATTTGA AAATGGACAG AATGTGTCTC AGGAAAAACA GCTAGTAGAC ATGAATTTTA       939
AATAATGTAT TTACTTTTTA TTTGCAACTT TAGTTTGTGT TATTATTTTT TAATAAGAAC       999
ATTAATTATA TGTATATTGT CTAGTAATTG GGAAAAAAGC AACTGGTTAG GTAGCAACAA      1059
CAGAAGGGAA ATTTCAATAA CCTTTCACTT AAGTATTGTC ACCAGGATTA CTAGTCAAAC      1119
AAAAAAGAAA AGTAGAAAGG AGGTTAGGTC TTAGGAATTG AATTAATAAT AAAGCTACCA      1179
TTTATCAAGC ATTTACCATG TGCTAATAAG TTTGAAATAT ATTATTTCCT TTATTCCTTT      1239
CAGCAATCCA TGAGATAGCT ATTATAATCC TC                                    1271
```

| 1 | cDNA | M D G N S T R S P E T N G L L C G D P E |
| | BTC-I | M D G N X T R S P E T N G L L X G D P E |

| 21 | | E N C A A T T T Q S K R K G H F S R C P |
| | BTC-II | R K G X F S R X P |

| 41 | | K Q Y K H Y C I K G R C R F V V A E Q T |
| | | K Q Y K H Y X I K G R |

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:1:

```
Asp  Gly  Xaa  Thr  Xaa  Arg  Thr  Pro  Glu  Thr  Asn  Gly  Ser  Leu  Xaa  Gly
 1             5                             10                            15

Ala  Pro  Gly  Glu  Glu  Arg  Thr  Arg
              20
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( D ) TOPOLOGY: linear (x i) SEQUENCE DESCRIPTION: SEQ ID NO:2:

```
Asp Gly Xaa Thr Xaa Arg Thr Pro Glu Xaa Asn Gly Ser Leu Xaa Xaa
 1               5                   10                  15
Ala Pro Xaa Xaa Xaa Xaa Xaa Xaa
            20
```

(2) INFORMATION FOR SEQ ID NO:3:

(i) SEQUENCE CHARACTERISTICS:
        (A) LENGTH: 48 amino acids
        (B) TYPE: amino acid
        (D) TOPOLOGY: linear (x i) SEQUENCE DESCRIPTION: SEQ ID NO:3:

```
Thr His Phe Ser Arg Cys Pro Lys Gln Tyr Lys His Tyr Cys Ile His
 1               5                   10                  15
Gly Arg Cys Arg Phe Val Val Asp Glu Gln Thr Pro Ser Cys Ile Cys
            20                  25                  30
Glu Lys Gly Tyr Phe Gly Ala Arg Cys Glu Arg Val Asp Leu Phe Tyr
            35                  40                  45
```

(2) INFORMATION FOR SEQ ID NO:4:

(i) SEQUENCE CHARACTERISTICS:
        (A) LENGTH: 1179 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (v i) ORIGINAL SOURCE:
        (A) ORGANISM: Mouse
        (B) STRAIN: BTC-JC10
        (G) CELL TYPE: Tumor Cell (i x) FEATURE:
        (A) NAME/KEY: CDS
        (B) LOCATION: 113..643

(i x) FEATURE:
        (A) NAME/KEY: mat peptide
        (B) LOCATION: 206..643

(x i) SEQUENCE DESCRIPTION: SEQ ID NO:4:

```
GAATTCGCGG CCGCGTTTTC AAGCACCCTC TCGGTGCCAG GGCCCAGGAA GGGCATAGAG          60

AAGGAACCTG AGGACTCATC CAGGGGCTGC CCTGCCCCTC ACAGCACAGT TG ATG            115
                                                           Met
                                                           -31

GAC CCA ACA GCC CCG GGT AGC AGT GTC AGC TCC CTG CCG CTG CTC CTG          163
Asp Pro Thr Ala Pro Gly Ser Ser Val Ser Ser Leu Pro Leu Leu Leu
-30              -25                 -20                 -15

GTC CTT GCC CTG GGT CTT GCA ATT CTC CAC TGT GTG GTA GCA GAT GGG          211
Val Leu Ala Leu Gly Leu Ala Ile Leu His Cys Val Val Ala Asp Gly
                 -10                 -5                  1

AAC ACA ACC AGA ACA CCA GAA ACC AAT GGC TCT CTT TGT GGA GCT CCT          259
Asn Thr Thr Arg Thr Pro Glu Thr Asn Gly Ser Leu Cys Gly Ala Pro
             5                   10                  15

GGG GAA AAC TGC ACA GGT ACC ACC CCT AGA CAG AAA GTG AAA ACC CAC          307
Gly Glu Asn Cys Thr Gly Thr Thr Pro Arg Gln Lys Val Lys Thr His
        20                  25                  30

TTC TCT CGG TGC CCC AAG CAG TAC AAG CAT TAC TGC ATC CAT GGG AGA          355
Phe Ser Arg Cys Pro Lys Gln Tyr Lys His Tyr Cys Ile His Gly Arg
```

-continued

| | | | | | | | | | | | | | | | | |
|---|---|---|---|---|---|---|---|---|---|---|---|---|---|---|---|---|
| 35 | | | | 40 | | | | | 45 | | | | | 50 | | |
| TGC | CGC | TTC | GTG | GTG | GAC | GAG | CAA | ACT | CCC | TCC | TGC | ATC | TGT | GAG | AAA | 403 |
| Cys | Arg | Phe | Val | Val | Asp | Glu | Gln | Thr | Pro | Ser | Cys | Ile | Cys | Glu | Lys | |
| | | | | 55 | | | | | 60 | | | | | 65 | | |
| GGC | TAC | TTT | GGG | GCT | CGG | TGT | GAG | CGA | GTG | GAC | CTG | TTT | TAC | CTC | CAG | 451 |
| Gly | Tyr | Phe | Gly | Ala | Arg | Cys | Glu | Arg | Val | Asp | Leu | Phe | Tyr | Leu | Gln | |
| | | | 70 | | | | | 75 | | | | | 80 | | | |
| CAG | GAC | CGG | GGG | CAG | ATC | CTG | GTG | GTC | TGC | TTG | ATA | GTG | GTC | ATG | GTG | 499 |
| Gln | Asp | Arg | Gly | Gln | Ile | Leu | Val | Val | Cys | Leu | Ile | Val | Val | Met | Val | |
| | | 85 | | | | | 90 | | | | | 95 | | | | |
| GTG | TTC | ATC | ATT | TTA | GTC | ATC | GGC | GTC | TGC | ACC | TGC | TGT | CAT | CCT | CTT | 547 |
| Val | Phe | Ile | Ile | Leu | Val | Ile | Gly | Val | Cys | Thr | Cys | Cys | His | Pro | Leu | |
| | 100 | | | | | 105 | | | | | 110 | | | | | |
| CGG | AAA | CAT | CGT | AAA | AAA | AAG | AAG | GAA | GAG | AAA | ATG | GAG | ACT | TTG | GAT | 595 |
| Arg | Lys | His | Arg | Lys | Lys | Lys | Lys | Glu | Glu | Lys | Met | Glu | Thr | Leu | Asp | |
| 115 | | | | | 120 | | | | | 125 | | | | | 130 | |
| AAA | GAT | AAA | ACT | CCC | ATA | AGT | GAA | GAT | ATT | CAA | GAG | ACC | AAT | ATT | GCT | 643 |
| Lys | Asp | Lys | Thr | Pro | Ile | Ser | Glu | Asp | Ile | Gln | Glu | Thr | Asn | Ile | Ala | |
| | | | | 135 | | | | | 140 | | | | | 145 | | |

| | | | | | |
|---|---|---|---|---|---|
| TAACGGTTAT | AAAGTTATCA | CAAGCTGGTG | GCAAGCTACA | AAAGACCTGA | CTCATTCCCA | 703 |
| GATGGACAGG | ACATGTCTCA | GGAAAACAGC | TAGCAGAAAT | GAATGTTTAA | ATATTGTATT | 763 |
| TACTTTTTTT | ATTTGTAACT | GTGTGTTGCT | TGTTATTGTT | TTTAATAACG | ATATATTTTT | 823 |
| TTTGTTACAG | CCTAGTAGTT | GAGAAAAAAT | AACCTGGTTA | GGTGATGACA | AAAATAAGGG | 883 |
| ACATTTGAAT | ATAAACTTTG | TTGCCAGGAT | TATTAAATAA | ATAAAGAAA | AGTGGAAAAG | 943 |
| AAGTTAGATT | TTTAAGAACT | AATTCACCAC | CACGCAATGG | TAGTACATGC | CTTTAATCCC | 1003 |
| AGGACTTGGG | AGGCAGAGGC | AGGCAAATCT | CTGTGAGTTC | AAGGCCAGCC | TGGTCTACAA | 1063 |
| AGAAAGTTCC | AAAATAGCCA | AGACTACAAC | AGAGGAACAC | TGTCTCAAAA | AACCTAACCA | 1123 |
| ACCAACCAAC | CAAACAAGCA | AGCAAACCC | TGTCAATAAT | AGGCGGCCGC | GAATTC | 1179 |

( 2 ) INFORMATION FOR SEQ ID NO:5:

( i ) SEQUENCE CHARACTERISTICS:
            ( A ) LENGTH: 1271 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( v i ) ORIGINAL SOURCE:
            ( A ) ORGANISM: Human
            ( B ) STRAIN: MCF7
            ( G ) CELL TYPE: Breast Adenocarcinoma Cell ( i x ) FEATURE:
            ( A ) NAME/KEY: CDS
            ( B ) LOCATION: 295..829

( i x ) FEATURE:
            ( A ) NAME/KEY: mat peptide
            ( B ) LOCATION: 388..829

( x i ) SEQUENCE DESCRIPTION: SEQ ID NO:5:

| | | | | | |
|---|---|---|---|---|---|
| CAGCGTGGAG | GCTCCAAGGA | CCAAGTCCTG | CGCCTCTTTG | GCGGGGTGTG | TGCAGGAGGA | 60 |
| GGGGGGATAA | ATAGGAGGCT | CCCTCCTCCC | GGCGACATTC | ACGGAGCCGG | CCGGCCTCCC | 120 |
| GCCCTGGGTG | TTTCCCTGCC | TTGTAGCCAG | GGTGCCAGCC | TGGGAAGTAG | TTTCGTTTCC | 180 |
| TTCTGCCTCC | GGGATTAGTT | TCCAGGCACC | CTCTCAGGCG | CCCGAGGCCC | GGGAAGGGGG | 240 |

| | | | | | | | | | | | | | | | |
|---|---|---|---|---|---|---|---|---|---|---|---|---|---|---|---|
| CGAAGAAGGA | | | GGGAGACTTG | | | TCTAGGGGCT | | | GCCCGGCCCG | | | GCAGAGCGGG | GTTG | ATG Met -31 | 297 |
| GAC Asp -30 | CGG Arg | GCC Ala | GCC Ala | CGG Arg | TGC Cys -25 | AGC Ser | GGC Gly | GCC Ala | AGC Ser | TCC Ser -20 | CTG Leu | CCA Pro | CTG Leu | CTC Leu | CTG Leu -15 | 345 |
| GCC Ala | CTT Leu | GCC Ala | CTG Leu | GGT Gly -10 | CTA Leu | GTG Val | ATC Ile | CTT Leu | CAC His -5 | TGT Cys | GTG Val | GTG Val | GCA Ala | GAT Asp | GGG Gly 1 | 393 |
| AAT Asn | TCC Ser | ACC Thr 5 | AGA Arg | AGT Ser | CCT Pro | GAA Glu | ACT Thr 10 | AAT Asn | GGC Gly | CTC Leu | CTC Leu | TGT Cys 15 | GGA Gly | GAC Asp | CCT Pro | 441 |
| GAG Glu | GAA Glu 20 | AAC Asn | TGT Cys | GCA Ala | GCT Ala | ACC Thr 25 | ACC Thr | ACA Thr | CAA Gln | TCA Ser | AAG Lys 30 | CGG Arg | AAA Lys | GGC Gly | CAC His | 489 |
| TTC Phe 35 | TCT Ser | AGG Arg | TGC Cys | CCC Pro | AAG Lys 40 | CAA Gln | TAC Tyr | AAG Lys | CAT His | TAC Tyr 45 | TGC Cys | ATC Ile | AAA Lys | GGG Gly | AGA Arg 50 | 537 |
| TGC Cys | CGC Arg | TTC Phe | GTG Val | GTG Val 55 | GCC Ala | GAG Glu | CAG Gln | ACG Thr | CCC Pro 60 | TCC Ser | TGT Cys | GTC Val | TGT Cys | GAT Asp 65 | GAA Glu | 585 |
| GGC Gly | TAC Tyr | ATT Ile | GGA Gly 70 | GCA Ala | AGG Arg | TGT Cys | GAG Glu | AGA Arg 75 | GTT Val | GAC Asp | TTG Leu | TTT Phe | TAC Tyr 80 | CTA Leu | AGA Arg | 633 |
| GGA Gly | GAC Asp | AGA Arg 85 | GGA Gly | CAG Gln | ATT Ile | CTG Leu | GTG Val 90 | ATT Ile | TGT Cys | TTG Leu | ATA Ile | GCA Ala 95 | GTT Val | ATG Met | GTA Val | 681 |
| GTT Val | TTT Phe 100 | ATT Ile | ATT Ile | TTG Leu | GTC Val | ATC Ile 105 | GGT Gly | GTC Val | TGC Cys | ACA Thr | TGC Cys 110 | TGT Cys | CAC His | CCT Pro | CTT Leu | 729 |
| CGG Arg 115 | AAA Lys | CGT Arg | CGT Arg | AAA Lys | AGA Arg 120 | AAG Lys | AAG Lys | AAA Lys | GAA Glu | GAA Glu 125 | GAA Glu | ATG Met | GAA Glu | ACT Thr | CTG Leu 130 | 777 |
| GGT Gly | AAA Lys | GAT Asp | ATA Ile | ACT Thr 135 | CCT Pro | ATC Ile | AAT Asn | GAA Glu | GAT Asp 140 | ATT Ile | GAA Glu | GAG Glu | ACA Thr | AAT Asn 145 | ATT Ile | 825 |
| GCT Ala | T | AAAAGGCTAT | | | GAAGTTACCT | | | CCAGGTTGGT | | | GGCAAGCTGC | | | AAAGTGCCTT | | 879 |
| GCTCATTTGA | | | AAATGGACAG | | | AATGTGTCTC | | | AGGAAAAACA | | | GCTAGTAGAC | | | ATGAATTTTA | 939 |
| AATAATGTAT | | | TTACTTTTTA | | | TTTGCAACTT | | | TAGTTTGTGT | | | TATTATTTTT | | | TAATAAGAAC | 999 |
| ATTAATTATA | | | TGTATATTGT | | | CTAGTAATTG | | | GGAAAAAGC | | | AACTGGTTAG | | | GTAGCAACAA | 1059 |
| CAGAAGGGAA | | | ATTTCAATAA | | | CCTTTCACTT | | | AAGTATTGTC | | | ACCAGGATTA | | | CTAGTCAAAC | 1119 |
| AAAAAGAAA | | | AGTAGAAAGG | | | AGGTTAGGTC | | | TTAGGAATTG | | | AATTAATAAT | | | AAAGCTACCA | 1179 |
| TTTATCAAGC | | | ATTTACCATG | | | TGCTAATAAG | | | TTTGAAATAT | | | ATTATTTCCT | | | TTATTCCTTT | 1239 |
| CAGCAATCCA | | | TGAGATAGCT | | | ATTATAATCC | | | TC | | | | | | | 1271 |

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: NO ( i x ) FEATURE:
        ( A ) NAME/KEY:

(B) LOCATION: 3 and 6
(C) OTHER INFORMATION: /note ="N = Inosine"

(ix) FEATURE:
(A) NAME/KEY:
(B) LOCATION: 11
(C) OTHER INFORMATION: /note ="N = A, G, T or C"

(xi) SEQUENCE DESCRIPTION: SEQ ID NO:6:

ACNCCNGARA CNAATGG                          17

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: unknown
(D) TOPOLOGY: unknown (ii) MOLECULE TYPE: DNA (genomic)

(ix) FEATURE:
(A) NAME/KEY:
(B) LOCATION: 18
(C) OTHER INFORMATION: /note ="N = A, G, T, or C"

(ix) FEATURE:
(A) NAME/KEY:
(B) LOCATION: 3, 6 and 9
(C) OTHER INFORMATION: /note ="N = Inosine"

(xi) SEQUENCE DESCRIPTION: SEQ ID NO:7:

GCNCCNGGNG ARGARMGNAC                       20

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:8:

CCRTGDATRC ARTARTG                          17

(2) INFORMATION FOR SEQ ID NO:9:

(i) SEQUENCE CHARACTERISTICS:
(A) LENGTH: 17 base pairs
(B) TYPE: nucleic acid
(C) STRANDEDNESS: unknown
(D) TOPOLOGY: unknown (ii) MOLECULE TYPE: DNA (genomic)

(ix) FEATURE:
(A) NAME/KEY:
(B) LOCATION: 3 and 15
(C) OTHER INFORMATION: /note ="N = A, G, T, or C"

(xi) SEQUENCE DESCRIPTION: SEQ ID NO:9:

GGNGTYTGYT CRTCNAC                          17

(2) INFORMATION FOR SEQ ID NO:10:

(i) SEQUENCE CHARACTERISTICS:
(A) LENGTH: 22 base pairs
(B) TYPE: nucleic acid
(C) STRANDEDNESS: unknown
(D) TOPOLOGY: unknown ( i i ) MOLECULE TYPE: DNA (genomic)

( x i ) SEQUENCE DESCRIPTION: SEQ ID NO:10:

ATACATATGG ATGGGAATTC CA 22

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:11:

CCGGATCCTA GTAAAACAAG TCAACTCT 28

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

TATGGATGGG 10

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

AATTCCCATC CA 12

( 2 ) INFORMATION FOR SEQ ID NO:14:

( i ) SEQUENCE CHARACTERISTICS:
        ( A ) LENGTH: 60 amino acids
        ( B ) TYPE: amino acid
        ( D ) TOPOLOGY: linear ( x i ) SEQUENCE DESCRIPTION: SEQ ID NO:14:

```
Met  Asp  Gly  Asn  Ser  Thr  Arg  Ser  Pro  Glu  Thr  Asn  Gly  Leu  Leu  Cys
 1                  5                        10                       15
Gly  Asp  Pro  Glu  Glu  Asn  Cys  Ala  Ala  Thr  Thr  Thr  Gln  Ser  Lys  Arg
               20                       25                       30
Lys  Gly  His  Phe  Ser  Arg  Cys  Pro  Lys  Gln  Tyr  Lys  His  Tyr  Cys  Ile
          35                            40                       45
Lys  Gly  Arg  Cys  Arg  Phe  Val  Val  Ala  Glu  Gln  Thr
     50                       55                       60
```

( 2 ) INFORMATION FOR SEQ ID NO:15:

( i ) SEQUENCE CHARACTERISTICS:
        ( A ) LENGTH: 20 amino acids
        ( B ) TYPE: amino acid -continued (D) TOPOLOGY: linear (xi) SEQUENCE DESCRIPTION: SEQ ID NO:15:

| Met | Asp | Gly | Asn | Xaa | Thr | Arg | Ser | Pro | Glu | Thr | Asn | Gly | Leu | Leu | Xaa |
|---|---|---|---|---|---|---|---|---|---|---|---|---|---|---|---|
| 1 |  |  |  | 5 |  |  |  |  | 10 |  |  |  |  | 15 |  |

| Gly | Asp | Pro | Glu |
|---|---|---|---|
|  |  |  | 20 |

(2) INFORMATION FOR SEQ ID NO:16:

(i) SEQUENCE CHARACTERISTICS:
(A) LENGTH: 20 amino acids
(B) TYPE: amino acid
(D) TOPOLOGY: linear (xi) SEQUENCE DESCRIPTION: SEQ ID NO:16:

| Arg | Lys | Gly | Xaa | Phe | Ser | Arg | Xaa | Pro | Lys | Gln | Tyr | Lys | His | Tyr | Xaa |
|---|---|---|---|---|---|---|---|---|---|---|---|---|---|---|---|
| 1 |  |  |  | 5 |  |  |  |  | 10 |  |  |  |  | 15 |  |

| Ile | Lys | Gly | Arg |
|---|---|---|---|
|  |  |  | 20 |

(2) INFORMATION FOR SEQ ID NO:17:

(i) SEQUENCE CHARACTERISTICS:
(A) LENGTH: 177 amino acids
(B) TYPE: amino acid
(D) TOPOLOGY: linear (xi) SEQUENCE DESCRIPTION: SEQ ID NO:17:

|  |  |  |  |  |  |  |  |  |  |  |  |  |  |  | Met |
|---|---|---|---|---|---|---|---|---|---|---|---|---|---|---|---|
|  |  |  |  |  |  |  |  |  |  |  |  |  |  |  | -31 |

| Asp | Pro | Thr | Ala | Pro | Gly | Ser | Ser | Val | Ser | Ser | Leu | Pro | Leu | Leu | Leu |
|---|---|---|---|---|---|---|---|---|---|---|---|---|---|---|---|
| -30 |  |  |  |  | -25 |  |  |  |  | -20 |  |  |  |  | -15 |

| Val | Leu | Ala | Leu | Gly | Leu | Ala | Ile | Leu | His | Cys | Val | Val | Ala | Asp | Gly |
|---|---|---|---|---|---|---|---|---|---|---|---|---|---|---|---|
|  |  |  |  | -10 |  |  |  |  | -5 |  |  |  |  |  | 1 |

| Asn | Thr | Thr | Arg | Thr | Pro | Glu | Thr | Asn | Gly | Ser | Leu | Cys | Gly | Ala | Pro |
|---|---|---|---|---|---|---|---|---|---|---|---|---|---|---|---|
|  |  | 5 |  |  |  |  | 10 |  |  |  |  | 15 |  |  |  |

| Gly | Glu | Asn | Cys | Thr | Gly | Thr | Thr | Pro | Arg | Gln | Lys | Val | Lys | Thr | His |
|---|---|---|---|---|---|---|---|---|---|---|---|---|---|---|---|
|  | 20 |  |  |  |  | 25 |  |  |  |  | 30 |  |  |  |  |

| Phe | Ser | Arg | Cys | Pro | Lys | Gln | Tyr | Lys | His | Tyr | Cys | Ile | His | Gly | Arg |
|---|---|---|---|---|---|---|---|---|---|---|---|---|---|---|---|
| 35 |  |  |  |  | 40 |  |  |  |  | 45 |  |  |  |  | 50 |

| Cys | Arg | Phe | Val | Val | Asp | Glu | Gln | Thr | Pro | Ser | Cys | Ile | Cys | Glu | Lys |
|---|---|---|---|---|---|---|---|---|---|---|---|---|---|---|---|
|  |  |  |  | 55 |  |  |  |  | 60 |  |  |  |  | 65 |  |

| Gly | Tyr | Phe | Gly | Ala | Arg | Cys | Glu | Arg | Val | Asp | Leu | Phe | Tyr | Leu | Gln |
|---|---|---|---|---|---|---|---|---|---|---|---|---|---|---|---|
|  |  |  | 70 |  |  |  |  | 75 |  |  |  |  | 80 |  |  |

| Gln | Asp | Arg | Gly | Gln | Ile | Leu | Val | Val | Cys | Leu | Ile | Val | Val | Met | Val |
|---|---|---|---|---|---|---|---|---|---|---|---|---|---|---|---|
|  |  | 85 |  |  |  |  | 90 |  |  |  |  | 95 |  |  |  |

| Val | Phe | Ile | Ile | Leu | Val | Ile | Gly | Val | Cys | Thr | Cys | Cys | His | Pro | Leu |
|---|---|---|---|---|---|---|---|---|---|---|---|---|---|---|---|
|  |  |  | 100 |  |  |  |  | 105 |  |  |  |  | 110 |  |  |

| Arg | Lys | His | Arg | Lys | Lys | Lys | Lys | Glu | Glu | Lys | Met | Glu | Thr | Leu | Asp |
|---|---|---|---|---|---|---|---|---|---|---|---|---|---|---|---|
| 115 |  |  |  |  | 120 |  |  |  |  | 125 |  |  |  |  | 130 |

| Lys | Asp | Lys | Thr | Pro | Ile | Ser | Glu | Asp | Ile | Gln | Glu | Thr | Asn | Ile | Ala |
|---|---|---|---|---|---|---|---|---|---|---|---|---|---|---|---|
|  |  |  |  | 135 |  |  |  |  | 140 |  |  |  |  | 145 |  |

(2) INFORMATION FOR SEQ ID NO:18:

(i) SEQUENCE CHARACTERISTICS:
(A) LENGTH: 178 amino acids
(B) TYPE: amino acid
(D) TOPOLOGY: linear (xi) SEQUENCE DESCRIPTION: SEQ ID NO:18:

```
                                                                        Met
                                                                        -31
Asp Arg Ala Ala Arg Cys Ser Gly Ala Ser Ser Leu Pro Leu Leu Leu
-30                 -25                 -20                         -15
Ala Leu Ala Leu Gly Leu Val Ile Leu His Cys Val Val Ala Asp Gly
                -10              -5                        1
Asn Ser Thr Arg Ser Pro Glu Thr Asn Gly Leu Leu Cys Gly Asp Pro
            5                10                      15
Glu Glu Asn Cys Ala Ala Thr Thr Thr Gln Ser Lys Arg Lys Gly His
    20                  25                      30
Phe Ser Arg Cys Pro Lys Gln Tyr Lys His Tyr Cys Ile Lys Gly Arg
35                  40                  45                      50
Cys Arg Phe Val Val Ala Glu Gln Thr Pro Ser Cys Val Cys Asp Glu
                55                  60                      65
Gly Tyr Ile Gly Ala Arg Cys Glu Arg Val Asp Leu Phe Tyr Leu Arg
            70                  75                  80
Gly Asp Arg Gly Gln Ile Leu Val Ile Cys Leu Ile Ala Val Met Val
        85                  90                  95
Val Phe Ile Ile Leu Val Ile Gly Val Cys Thr Cys Cys His Pro Leu
    100             105             110
Arg Lys Arg Arg Lys Arg Lys Lys Glu Glu Glu Met Glu Thr Leu
115             120             125                     130
Gly Lys Asp Ile Thr Pro Ile Asn Glu Asp Ile Glu Glu Thr Asn Ile
            135             140                     145
Ala
```

SMOOTH MUSCLE MITOGEN PEPTIDES AND DNA CODING THEREFOR

This is a continuation of application Ser. No. 08/007,126 filed on Jan. 21, 1993, now abandoned, which is a continuation-in-part application of U.S. application Ser. No. 07/994,776, filed on Dec. 22, 1992, now abandoned, U.S. application Ser. Nos. 07/872,597 and 07/872,792, filed Apr. 23, 1992, now abandoned, which are continuation-in-part applications of U.S. application Ser. Nos. 07/833,552 and 07/832,939, respectively, filed on Feb. 10, 1992, now abandoned, which are continuation-in-part applications of U.S. application Ser. No. 07/766,354, filed Sep. 26, 1991, now abandoned, which is a continuation-in-part application of U.S. application Ser. No. 07/604,778, filed Oct. 26, 1990 now U.S. Pat. No. 5,229,493 granted Jul. 20, 1993.

This invention was made with U.S. Government support and the Government has certain rights in the invention.

The present invention is directed to a recombinant non-glycosylated mammalian growth factor which stimulates the growth of smooth muscle cells and to the uses thereof.

BACKGROUND OF THE INVENTION

While smooth muscle cell proliferation has been extensively studied, (see, e.g. Schwartz et al., Circulation Research, Vol. 58, No. 4, page 427, the disclosure of which is incorporated by reference herein), the signals controlling the proliferation of smooth muscle cells remain largely unknown. Smooth muscle cell proliferation is known to play a central role in diseases such as arteriosclerosis (atherosclerosis and hypertension). Lack of smooth muscle proliferation in infants also plays a role in vascular malformations. This failure of smooth muscle cell replication results in untreatable vascular lesions which often lead to death.

Although it is now generally acknowledged that proliferation of smooth muscle cells occurs during formation of atherosclerotic lesions, the role of that proliferation response in the overall history of the plaque is not all obvious. A few investigators have suggested that replication occurring during development of arteries is the initial event in formation of atherosclerotic lesions, preceding lipid accumulation or endothelial injury.

The major hypothesis explaining smooth muscle replication in the vessel wall is the response-to-injury hypothesis. In brief, hypothesis is that smooth muscle cells in the wall normally exist in a quiescent state. When the endothelium is injured, platelets release a factor or factors that stimulate smooth muscle cell movement into and replication within the arterial intima (Ross, Arteriosclerosis 1:293–311, 1981). Ross also showed the cultured smooth muscle cells require a platelet derived growth factor (PDGF) for proliferation (Ross and Glomset, N. Eng. J. Med. 295; 369–377 and 420–425, 1976). The apparent conclusion is that platelet release is necessary for smooth muscle proliferative response to balloon denudation.

Ross's observation led to the ensuing purification of the PDGF, identification of its receptor and, more recently, identification of the oncogene c-sis as the gene for one of the two PDGF peptide chains.

The second known requirement for cell cycle progression is availability of somatomedin C., also known as insulin-like growth factor (IGF-1). IGF-1 itself can be synthesized by smooth muscle cells, and antibodies to IGF-1 inhibit cell cycle progression. These data suggest that PDGF is capable of stimulating production of its own progression factor. This observation is of considerable importance to the interesting possibility that smooth muscle replication may be controlled by factors intrinsic to the vessel wall.

Other substances mitogenic for smooth muscle cells, apart from PDGF have also been studied. In addition, platelets also contain a protein resembling epidermal growth factor (EGF) (Oka and Orth, J. Clin. Invest. 72:249–259, 1983) and Assoian et al., 1984) and a factor able to assist growth of cell in suspension called β tumor growth factor (Tucker et al., Science 226: 705–777, 1984). The relative contribution of each of these to stimulation of proliferation is largely unknown.

The stimuli controlling smooth muscle replication in hypertension also remains largely unknown. PDGF may play an important role in microvascular changes in malignant hypertension, but is not likely to be involved in large vessels or in any vessel affected by milder and more chronic forms of high blood pressure.

While there has been much research on the role of smooth muscle in various disease pathologies, and several mechanisms and roles of growth factors such as PDGF have been explored, there continues to be a need for new information about mitogens which stimulate the proliferation of smooth muscle cells. The identification of such mitogens will permit various treatment strategies to be devised such as competitive binding strategies employing antibodies to the smooth muscle mitogen or competitive proteins which will bind to the receptors for such mitogens. Smooth muscle mitogens may also be used in the treatment of conditions such as vascular malformation or as a growth factor in wound/ulcer healing.

SUMMARY OF THE INVENTION

In the above-referenced parent applications, there is disclosed a novel growth factor (hereinafter "BTC-GF") obtainable from the conditioned medium of pancreatic tumor cells initially derived from transgenic mice (RIP1-Tag 2) in which virtually every beta cell expressed the oncogene SV40 large T. A sample of the pancreatic tumor cells (hereinafter "BTC-3 cells") from which BTC-GF was originally identified, isolated and purified has been deposited at the American Type Culture Collection under the Budapest Treaty on Oct. 26, 1990 under ATCC Accession No. CRL 10585. BTC-GF may also be purified from a subline of pancreatic tumor cells (hereinafter "BTC-JC10 cells"), a sample of which has been deposited at the American Type Culture Collection under the Budapest Treaty on Sep. 24, 1991 under ATCC Accession No. CRL 10875.

BTC-GF is a mitogen for smooth muscle cells, 3T3 fibroblasts, and retinal pigment epithelial cells, but not for endothelial cells. BTC-GF is not inactivated by boiling, by 10 mM dithiothreitol or by exposure to 1M acetic acid. The biological activity of BTC-GF is present as a single band of protein having a molecular weight of about 32,000 on SDS-PAGE. The partial N-terminal amino acid sequence of BTC-GF as determined by comparing the N-terminal amino acid sequence of BTC-GF purified from both BTC-3 (SEQ ID NO:2) and BTC-JC10 (SEQ ID NO:1) cells and by deduction from the nucleotide sequence of BTC-GF cDNA is:

Asp-Gly-Asn-Thr-Thr-Arg-Thr-Pro-Glu-Thr-Asn-Gly-Ser-Leu-Cys-Gly-Ala-Pro-Gly-Glu-Asn-Cys-Thr-Gly (which correspond to amino acid sequence nos. 1–24 of SEQ ID NO:17) (see FIGS. 7 and 9).

A computer search through translated GENBANK and NBRF Protein Database failed to reveal any similar proteins.

BTC-GF can be used in the treatment of diseases such as vascular malformation as well as in the treatment of wounds/ ulcers and the like. BTC-GF may also be used to produce competitive agents such as antibodies or false peptides. Because, BTC-GF is derived from the insulin-producing cells of the islet, such competitive agents may be used in the treatment of diseases resulting from smooth muscle cell proliferation such as atherosclerosis and diabetic retinopathy that are observed in diabetes, as well as in hypertension. It may also be used as a diagnostic test in which, for example, an antibody to the growth factor can detect this factor in the blood of diabetics in whom dying or regenerating beta cells with islet are releasing the factor.

The present invention provides novel recombinant non-glycosylated mammalian BTC-GF, isolated DNA coding for mammalian BTC-GF, including isolated DNA coding for human BTC-GF and the expressed products therefrom.

BRIEF DESCRIPTION OF THE DRAWINGS

FIG. 7 illustrates the N-terminal amino acid sequence of mouse BTC-GF purified from BTC-3 (SEQ ID NO:2) and BTC-JC10 (SEQ ID NO:1) cells respectively.

FIG. 8 (SEQ ID NO:3) illustrates the internal amino acid sequence of mouse BTC-GF from amino acids 44–68.

FIG. 9 illustrates the base sequence of mouse BTC-GF cDNA and deduced amino acid sequence of mouse BTC-GF (SEQ ID NO:4 and SEQ ID NO:17).

FIG. 10 illustrates the base sequence and deduced amino acid sequence (SEQ ID NO:5 and SEQ ID NO:18) of human BTC-GF cDNA, obtained in Example 1 or the amino acids No. 1 to 80 of FIG. 10.

DETAILED DESCRIPTION OF THE INVENTION

Figure 1:
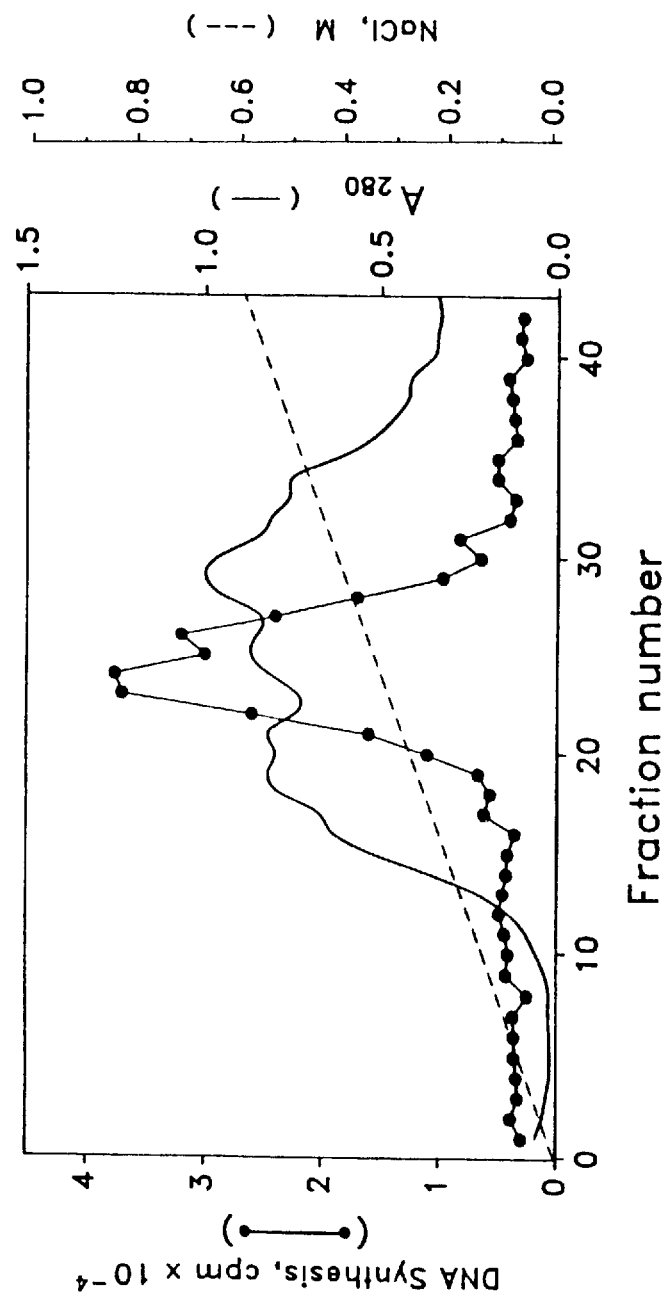
FIG. 1 illustrates the 3T3 cell growth factor activity of mouse BTC-GF after concentrated serum free beta tumor cell conditioned medium is passed through a Biorex 70 Cation Exchange Column.

In accordance with the present invention, there is provided a novel recombinant non-glycosylated mammalian growth factor BTC-GF which promotes the proliferation of smooth muscle cells and a method for producing it.

Native BTC-GF was identified and isolated from the conditioned medium of BTC-3 pancreatic tumor cells (ATCC No. CRL 10585) which were initially derived from transgenic mice (RIP1-Tag 2) in which virtually every beta cell expressed the oncogene SV40 T. BTC-GF has also been purified from BTC-JC10 cells (ATCC No. CRL 10875).

Native BTC-GF produced has a molecular weight of about 32,000 on SDS-PAGE and is heat stable when subjected to boiling. BTC-GF is also stable in the presence of 10 mM dithiothreitol and when exposed to 1M concentration of acetic acid.

While a number of methods may be employed in purifying the native BTC-GF, the preferred methods are outlined below.

First, the beta tumor cells are cultured in roller bottles in DMEM with 5% calf serum for four days. The medium is then replaced with serum free medium and cultured for 48–72 hours before harvest.

Next, serum free beta tumor cell conditioned medium is concentrated and passed through a number of columns such as a Biorex 70 column, a phenyl Sepharose column, and FPLC heparin affinity column, and an HPLC reverse phase column.

The N-terminal amino acid sequence of BTC-GF obtained by comparing BTC-GF from BTC-3 and BTC-JC10 cells as determined with an ABI 470A protein sequencer and by deduction from the nucleotide sequence of the cDNA encoding BTC-GF (FIG. 9 (SEQ ID NO:4)) is as follows:
Asp-Gly-Asn-Thr-Thr-Arg-Thr-Pro-Glu-Thr-Asn-Gly-Ser-Leu-Cys-Gly-Ala-Pro-Gly-Glu-Asn-Cys-Thr-Gly (which corresponds to amino acids 1–34 of SEQ ID NO:4).

The internal amino acid sequence (see FIG. 9 (SEQ ID NO:17), amino acids 44–66) of BTC-GF is as follows:
His-Tyr-Cys-Ile-His-Gly-Arg-Cys-Arg-Phe-Val-Val-Asp-Glu-Gln-Thr-Pro-Ser-Cys-Ile-Cys-Glu-Lys-(which corresponds to amino acid sequence Nos. 12–34 of SEQ ID NO:3).

The present inventors found that mouse BTC-GF can be produced by cloning mouse BTC-GF gene from mouse cells, constructing a recombinant DNA containing said mouse BTC-GF gene, and cultivating the transformant which resulted from transformation with said DNA.

In general, the proteins of animals which are closely related to humans have extremely high homology in amino acid sequence with the corresponding human proteins. In fact, portions of different amino acids are often derived by one-point mutation of the codons. It is therefore reasonable to expect that the DNA sequence of the above-mentioned mouse BTC-GF gene resembles the DNA sequence of the human BTC-GF gene. The present inventors found that human BTC-GF can be produced by cloning human BTC-GF gene from human cells using a part of the mouse BTC-GF gene as the DNA probe, constructing a recombinant DNA containing said human BTC-GF gene, and cultivating the transformant which resulted from transformation with said DNA.

The present inventors have made further study and have completed the present invention, which invention relates to:

(1) A recombinant non-glycosylated mammalian BTC-GF.

(2) Isolated DNA coding for mammalian BTC-GF.

(3) A recombinant vector which has the isolated DNA of said (2).

(4) A transformant which harbors the vector of said (3), and (5) A method for producing the BTC-GF protein of said (1), which comprises cultivating the transformant of said (4) in a culture medium.

As the recombinant non-glycosylated mammalian BTC-GF, Examples are a protein comprising human BTC-GF and mouse BTC-GF.

As the recombinant non-glycosylated human BTC-GF, there is exemplified a protein having an amino acid sequence comprising the amino acid No. 1 to 80, or the amino acid No. 1 to No. 147 of FIG. 10 (SEQ ID NO:18).

As the recombinant non-glycosylated mouse BTC-GF, there is exemplified a protein having an amino acid sequence comprising the amino acid No. 1 to 146 of FIG. 9 (SEQ ID NO:17).

Thus, in accordance with another embodiment of the present invention there is provided isolated DNA coding for BTC-GF, as well as a method for the production of BTC-GF by genetic engineering techniques.

More specifically, there is provided an expression vector which contains a DNA having a base sequence coding for the polypeptide of mammalian BTC-GF which may be produced, for example, by:

(a) Isolating an RNA coding for mammalian BTC-GF;

(b) Synthesizing a single-stranded complementary DNA (cDNA) based on said RNA and then synthesizing the corresponding double-stranded DNA and, if necessary, mutagenesis is carried out;

(c) Inserting said complementary DNA into a plasmid or a phage vector;

(d) Transforming a host with the resultant recombinant plasmid;

(e) Cultivating the transformant obtained or forming the phage-plaque and isolating that plasmid or phage DNA which contains the DNA as desired from the transformant or phage by an appropriate method, for example by the colony hybridization method or plaque hybridization method using a DNA probe;

(f) Excising the cloned, desired DNA from said plasmid or phage; and (g) Inserting said cloned DNA into a vehicle at a site downstream from a promoter.

RNAs coding for mammalian BTC-GF can be obtained from a variety of mammalian BTC-GF producing cells or pancreatic tumor cells as mentioned above.

One method for RNA preparation from mammalian BTC-GF-producing cells is the guanidine thiocyanate method [J. M. Chirgwin et al.: Biochemistry, 18, 5294 (1979)].

Using the thus-obtained RNA as a template together with reverse transcriptase, a cDNA may be synthesized for example by the method of H. Okayama et al. [Molecular and Cellular Biology, 2, 161 (1982)]. The cDNA obtained is inserted into a plasmid or a phage vector.

In addition to the above technique, site-directed mutagenesis may be employed. Site-directed mutagenesis is well-known, and it is described in Genetic Engineering, Lather, R. F. and Lecoq, J. P., Academic Press, pp. 31 to 50 (1983). Mutagenesis directed to oligonucleotides is described in Genetic Engineering; Principles and Methods, Smith, M. and Gillam, S., Plenum Press, vol. 3, pp. 1 to 32 (1981).

The production of the structural gene which encodes the present mammalian BTC-GF may be, for example, carried out by:

(a) hybridizing with a mutagenic oligonucleotide primer a single-stranded DNA comprising 1 strand of the structural gene, (b) elongating the primer using DNA polymerase to form a mutational heteroduplex, and (c) replicating this mutational heteroduplex.

The size of oligonucleotide primer depends upon conditions essential to stable hybridization of the primer to the gene region to which mutation is to be introduced, and upon limitations in currently available methods of oligonucleotide synthesis. The factors to be considered in designing the oligonucleotide intended for the use of mutagenesis directed by the oligonucleotide (e.g., the overall size of the nucleotide and the size of the mismatching portion at the mutation site) are described by Smith, M. and Gillam, S. in the above-mentioned literature. In general, the overall length of the oligonucleotide is adjusted to such length that stable and unique hybridization at the mutation site is optimized, and the extensions between the mutation site and the 5'-and 3'-terminals are provided with sufficient sizes to prevent mutation editing due to the exonuclease activity of DNA polymerase.

The oligonucleotides used for mutagenesis normally contain some 12 to 24 bases, preferably 14 to 20 bases, and more preferably 14 to 18 bases. These normally contain at least about 3 base 3'-terminal of the codons to be changed.

For the purpose of obtaining, for example, a mammalian BTC-GF having an added amino acid, a mutagenic mammalian BTC-GF gene is produced by synthesizing the gene which encodes the amino acid sequence to be added, and, directly or after fragmentation by digestion with restriction enzyme, inserting or adding it into an appropriate site in the mammalian BTC-GF gene using DNA ligase. When any suitable restriction enzyme recognition site is not present in the mammalian BTC-GF gene, restriction enzyme recognition sites may be produced by the above-mentioned site-directed mutagenesis.

For this purpose of obtaining, for example, a mammalian BTC-GF lacking constituent amino acids, a mutagenic mammalian BTC-GF gene is produced in that, for example, the carboxyl terminal is deleted.

In the case of deletion of an amino acid sequence in the carboxyl terminal side, a codon of the gene which encodes amino-terminal amino acids of the sequence to be deleted is changed to a stop codon by site-directed mutagenesis.

The plasmid into which said cDNA is to be inserted is, for example, a plasmid derived from *Escherichia coli* such as pBR322 [Gene, 2, 95 (1977)], pBR325 [Gene, 4, 121 (1978)], pUC12 [Gene, 19, 259 (1982)] or pUC13 [Gene, 19, 259 (1982)], or one derived from *Bacillus subtilis* such as pUB110 [Biochemical and Biophysical Research Communications, 112, 678 (1983)]. Any other plasmids capable of being replicated and maintained with the host employed may be used as well.

The phage vector into which said cDNA is to be inserted is, for example λgt10 or λgt11.

One preferred method for insertion into a plasmid, is the method described by T. Maniatis et al. in Molecular Cloning, Cold Spring Harbor Laboratory, page 239 (1982).

The plasmid obtained in this manner is introduced into an appropriate host, for example a bacterial strain belonging to the genus Escherichia or Bacillus.

Examples of the above strain of the genus Escherichia are *Escherichia coli* K12DH1 [Proc. Natl. Acad. Sci. USA, 60, 160 (1968)], M103 [Nucleic Acids Research, 9, 309 (1981)], JA221 [Journal of Molecular Biology, 120, 517 (1978)], HB101 [Journal of Molecular Biology, 41, 459 (1969)] and C600 [Genetics, 39, 440 (1954)], MM294 [Proc. Natl. Acad. Sci. USA, 73, 4174 (1976)].

Examples of the above strain of the genus Bacillus are *Bacillus subtilis* MI114 [Gene, 24, 255 (1983)] and 207–21 [Journal of Biochemistry, 95, 87 (1984)].

One preferred method for effecting transformation is the calcium chloride or calcium chloride/rubidium chloride method described by T. Maniatis et al. in Molecular Cloning, Cold Spring Harbor Laboratory, page 249 (1982).

From among the thus-obtained transformants, the desired clones may be selected, for example, by the colony hybridization method [Gene, 10, 63 (1980)] plus the DNA base sequence determination method [Proc. Natl. Acad. Sci. USA, 74, 560 (1977); Nucleic Acids Research, 9, 309 (1981)].

In this way, a microorganism which carries a vector having a cloned DNA encoding the BTC-GF or a phage having a cloned DNA encoding an BTC-GF is obtained.

The plasmid is isolated from said microorganism.

For such plasmid isolation, the alkaline extraction method [H. C. Birnboim et al.: Nucleic Acids Research, 1, 1513 (1979)], for instance, may be used.

The above-mentioned plasmid or phage vector having the cloned DNA encoding BTC-GF is used as it is or, as desired, subjected to restriction enzyme treatment for excision of said DNA.

Expression vectors can be obtained by inserting the cloned cDNA into a vehicle (vector) suited for expression of said cDNA at a site downstream of a promoter.

Said vector includes, among others, the above-mentioned *Escherichia coli*-derived plasmids (e.g. pBR322, pBR325, pUC13) and *Bacillus subtilis*-derived plasmids (e.g. pUB110, pTP5, pC194) as well as yeast-derived plasmids (e.g. pSH19, pSH15), bacteriophages such as λ phage, and animal viruses such as retroviruses and vaccinia virus.

Said cDNA may have ATG as the translational start codon at its 5' end. It may also have TAA, TGA or TAG as a translational termination codon at the 3' end. For effecting expression of said cDNA, a promoter is connected thereto at a site upstream from said cDNA. The promoter to be used in the practice of the invention may be any promoter if it is appropriate and adapted for the host employed for the expression of said cDNA.

When the host to be transformed is a strain belonging to the genus Escherichia, T7 phage promoter, the trp promoter, lac promoter, rec A promoter, λpL promoter and lpp promoter are preferred among others. When the host is a strain of the genus Bacillus, the SP01 promoter, SP02 promoter and penP promoter, for instance, are preferred. When the host is a yeast strain, the PH05 promoter, PGK promoter, GAP promoter and ADH promoter are preferred amongst others. In particular, it is preferable that the host should be a strain of the genus Escherichia and that the promoter should be the trp promoter or λpL promoter.

When the host is an animal cell line, SV40-derived promoters and retrovirus promoters are usable among others. In particular, SV40-derived promoters are preferable.

Using the vector thus obtained, a transformant can be produced by introducing it to a host cell.

Examples of the host include strains belonging to the genus Escherichia, strains belonging to the genus Bacillus, yeasts and animal cells. Representative examples of the strains of the genera Escherichia and Bacillus are those mentioned hereinbefore.

As the yeasts, *Saccharomyces cerevisiae* AH22R$^-$, NA87-11A and DKD-5D, may be used.

As the animal cells, preferred cell lines include monkey COS-7 [Gluzman, Y, cell 23, 157 (1981)] and Vero cells, Chinese hamster CHO cells, mouse L cells and human FL cells, among others.

The transformation of the above-strains of the genus Escherichia may be conducted, for example, by the method described in Proc. Natl. Acad. Sci. USA, 69, 2110 (1972) or in Gene, 17, 107 (1982), for instance.

The transformation of a strain of the genus Bacillus is performed, for example, by the method described in Molecular and General Genetics, 168, 111 (1979).

The transformation of yeasts is carried out, for example, by the method described in Proc. Natl. Acad. Sci. USA, 75, 1929 (1978).

The transformation of animal cells is conducted, for example, by the method described in Virology, 52, 456 (1973), among others.

In this manner, there are obtained transformants which are transformed with vectors containing the DNA encoding mammalian BTC-GF.

Said transformant is cultivated in a medium to allow it to produce mammalian BTC-GF.

The medium to be used in cultivating a transformant obtained with a strain of the genus Escherichia or Bacillus as the host is generally a liquid one which contains substances required for the growth of said transformant, for example, carbon and nitrogen sources and inorganic nutrients. Glucose, dextrin, soluble starch and sucrose, for instance, may serve as carbon sources. Ammonium salts, nitrate salts, corn steep liquor, peptone, casein, meat extract, soybean cake and potato extract may serve as nitrogen sources. As the inorganic nutrients, there may be mentioned calcium chloride, sodium dihydrogen phosphate and magnesium chloride, among others. Yeast extracts, vitamins, growth promoters and the like may further be added.

The medium should preferably have a pH of between about 6 to 8.

M9 medium containing glucose and casamino acids (Miller: Journal of Experiments in Molecular Genetics, 431–433, Cold Spring Harbor Laboratory, New York, 1972), is a preferred medium for use in cultivating microorganism of the genus Escherichia. For efficient performance of the promoter function, an agent such as 3-β-indolylacrylic acid in the case of trp promoter may be added as necessary.

When the host is microorganism of the genus Escherichia, the cultivation is conducted generally at about 15° to 43° C. for about 3 to 24 hours. If necessary, aeration and/or stirring may be made.

When the host is a microorganism of the genus Bacillus, the cultivation is performed generally at about 30° to 40° C. for about 6 to 24 hours. Aeration and/or stirring may be conducted as necessary.

When the host is a yeast transformant, Burkholder's minimum medium [Bostian, K. L. et al.: Proc. Natl. Acad. Sci. USA, 77, 4505 (1980)], for instance, may be used as the medium. The pH of the medium should preferably be adjusted to about 5 to 8. The cultivation is carried out generally at about 20° to 35° C. for about 24 to 72 hours, with aeration and/or stirring as necessary.

The preferred medium for cultivating an animal cell transformant includes MEM medium [Science, 122, 501 (1952)], DMEM medium [Virology, 8, 396 (1959)], RPMI 1640 medium [Journal of the American Medical Association, 199, 519 (1967)] or 199 medium [Proceedings of the Society for the Biological Medicine, 73, 1 (1950)], which is further added about 5 to 20% of fetal calf serum. The medium should preferably have a pH of about 6 to 8. The cultivation is carried out generally at about 30° to 40° C. for about 15 to 60 hours, with aeration and/or stirring as necessary.

Recombinant BTC-GF can be isolated in a purified form from the above cultivation product, for example by the following methods:

In extracting the BTC-GF from cultured cells, said cells after cultivation are collected and then processed by an appropriate method such as to the method comprising suspending the cells in a buffer solution containing a protein-denaturing agent such as guanidine hydrochloride to thereby cause extracellular dissolution of the desired protein or the method comprising disrupting the cells by French press, sonication, lysozyme treatment and/or freezing and thawing, followed by centrifugation for the recovery of the BTC-GF protein. The French press treatment or combined use of lysozyme treatment and sonication are particularly preferred.

For the purification of the BTC-GF from the supernatant obtained in the above manner, appropriate combinations of known isolation and purification methods can be used. Preferred isolation and purification methods include methods utilizing solubility differences, such as the salting-out method and solvent recipitation method, the methods utilizing molecular weight differences in the main, such as the dialysis method, ultrafiltration method, gel filtration method and SDS-polyacryl-amide gel electrophoresis method, the methods utilizing charge differences, such as the ion exchange chromatography method, methods utilizing specific affinities, such as the affinity chromatography method, methods utilizing hydrophobicity differences, such as reverse phase high performance liquid chromatography, and method utilizing isoelectric point differences, such as isoelectric focusing, among others.

More specifically, contaminant nucleic acids and acidic proteins can be removed from the above-mentioned supernatant by subjecting said supernatant to ion exchange chromatography using DEAE-cellulose, or the like. For example, it is efficient to apply the supernatant to a DEAE-cellulose column equilibrated with an almost neutral buffer (e.g. Tris buffer) and collect the effluent fraction. When said effluent fraction is subjected to ion exchange chromatography using CM-cellulose or the like, the BTC-GF, which is a basic protein, is absorbed on the carrier and can be eluted with a salt solution. CM-cellulose or the like acidic resin column chromatography can be used for the bacterial extract directly to purify BTC-GF.

For example, it is efficient to apply the supernatant to a CM-cellulose column equilibrated with a slightly acidic buffer (such as phosphate buffer). After washing the column with the same buffer, BTC-GF can be recovered by eluting the column with the buffer containing additional salts (such as NaCl). The eluate can be lyophilized after dialysis.

Affinity chromatography using heparin-Sepharose can be applied to purifying BTC-GF in *Escherichia coli* extracts. Thus, for instance, the BTC-GF protein can be purified by applying the above eluate to a heparin-Sepharose column equilibrated with an almost neutral buffer (e.g. Tris or phosphate buffer), washing the column thoroughly and performing elution by linear gradient constructed with NaCl or the like.

Heparin columns (e.g. Shodex AF-pak HR-894, available from Showa Denko, Japan) developed for high performance liquid chromatography are particularly efficient.

In this case, BTC-GF can be recovered as a homogeneous product in the same manner as in the case of the heparin-Sepharose column mentioned above, namely by applying the sample to a heparin column with an about neutral buffer, washing the column thoroughly and conducting elution on a linear gradient constructed with NaCl.

The thus-obtained product can be made up into a dry powder form by dialysis and lyophilization. To preserve the product with an added carrier (e.g. serum albumin) is desirable since the adsorption of the product on the vessel wall can be prevented thereby.

Furthermore, it is preferable to add a slight amount of a reducing agent in the course of purification or preservation, in order to prevent oxidation of the product.

Reducing agents which can be used include beta-mercaptoethanol, dithiothreitol, glutathione, and the like.

In this way, substantially pure BTC-GF can be obtained. The substantially pure BTC-GF according to this invention includes products whose BTC-GF content is not less than about 95% (w/w) and, more preferably, products whose BTC-GF content is not less than about 98% (w/w).

For its pharmaceutical use, the BTC-GF according to the present invention can be safely administered to warm-blooded animals (e.g. human, mouse, rat, hamster, rabbit, dog, cat) parenterally or orally either per se in a powder form or in the form of pharmaceutical compositions (e.g. injection, tablet, capsule, solution, ointment) made up together with pharmacologically acceptable carriers, excipients and/or diluents.

Injectable preparations can be produced by a conventional method using, for example, physiological saline or an aqueous solution containing glucose and/or other adjuvant or adjuvants. Tablets, capsules and other pharmaceutical compositions can be prepared as well by a conventional method.

The present recombinant non-glycosylated mammalian BTC-GF has the same biological activity as those of native BTC-GF.

Purified BTC-GF in accordance with the present invention can be used in the treatment of pathological conditions such as vascular malformation by intravascular infusion, or for the treatment of atherosclerosis by administration of a competitive inhibitor.

Purified BTC-GF can also be used in the treatment of wounds, ulcers and the like.

When BTC-GF of the present invention is used as in the treatment of diseases is vascular malformation as well as in the treatment of wounds/ulcers, the amount of the BTC-GF to be administered to the warm-blooded animals is small, and an appropriate amount is selected from 1 ng to 1 mg/kg more preferably 10 ng to 100 µg/kg a day according to the route of administration or symptoms.

Purified BTC-GF of the present invention can also be used to produce various competitive agents which can be used in the treatment of atherosclerosis and diabetic retinopathy, as well as in hypertension. Competitive agents such as antibodies or false proteins can be produced which will compete with and/or block BTC-GF from stimulating proliferation of smooth muscle cells.

BTC-GF can also be used to generate antibodies to itself. The antibody generated can be polyclonal or monoclonal depending upon the particular application for which it is designed. Such antibodies can be prepared by techniques well known to the skilled artisan. For example, the protein or antigenic portion thereof can be conjugated to keyhole limpet hemocyanin (KLH) and used to raise an antibody in an animal such as a rabbit. Typically, the peptide-KLH conjugate is injected several times over a period of about two months to generate antibodies. The antibody is then collected from serum by standard techniques. Alternatively, monoclonal antibodies can be produced in cells which produce antibodies to the protein by using standard fusion techniques for forming hybridoma cells. [Kohler, G., et al., *Nature* 256:495 (1975) which is incorporated by reference]. Typically, this involves fusing an antibody producing cell with an immortal cell line such as a myeloma cell to produce the hybrid cell. Alternatively, monoclonal antibodies can be produced from cells by the method of Huse, et al, *Science* 246:1275 (1989) which is incorporated herein by reference.

Usually, glycosylated protein is produced as heterogeneous form because of the heterogeneity of glycosylation of each molecule. In contrast, non-glycosylated protein is produced to be homogeneous, indicating that the purification of non-glycosylated proteins are easier than those of glycosylated molecules. In addition, most of the non-glycosylated proteins can be produced by prokaryotic expression systems. This means the productivity of non-glycosylated proteins is higher than those of glycosylated proteins.

In the specification, claims and drawings, the abbreviations used for bases, amino acids and so on are those recommended by the IUPAC-IUB Commission on Biochemical Nomenclature or those conventionally used in the art. Examples are given below. Amino acids for which optical isomerism is possible are, unless otherwise specified, in the L form.

DNA: Deoxyribonucleic acid
cDNA: Complementary deoxyribonucleic acid
A: Adenine
T: Thymine
G: Guanine
C: Cytosine
I: Inosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine The invention will be further illustrated by reference to the following examples which will aid in the understanding of the present invention, but which are not to be construed as a limitation thereof.

Growth factor activities discussed in the Examples and in Table 1 were assayed by measuring the incorporation of [methyl-$^3$H]thymidine into DNA of quiescent mouse Balb/c 3T3 cells as previously described (Shing Y., Davidson S. and Klagsbrun M. methods in Enzymology, 146B, 42–48, 1987) the disclosure of which is hereby incorporated by reference.

TABLE 1

Purification of BTC-GF

| Purification Step | Total Protein, mg | Total Activity, U | Specific Activity, U/mg | Activity Recovery | Purification Fold |
|---|---|---|---|---|---|
| Conditioned medium | 1360 | $24 \times 10^4$ | $1.7 \times 10^2$ | 100 | 1 |
| BioRex column | 52.7 | $6.5 \times 10^4$ | $1.2 \times 10^3$ | 27 | 7 |
| Heat, 100° C. (5 min.) | 15.5 | $5 \times 10^4$ | $3.2 \times 10^3$ | 21 | 19 |
| Phenyl column | 1.5 | $4 \times 10^4$ | $2.8 \times 10^4$ | 17 | 164 |
| Heparin column | 0.09 | $3 \times 10^4$ | $3.3 \times 10^5$ | 10 | 1,942 |
| C4 column, 1st | 0.0012* | $1.4 \times 10^4$ | $1.2 \times 10^7$ | 5.8 | 70,000 |
| C4 column, 2nd | 0.00034* | $0.98 \times 10^4$ | $2.9 \times 10^7$ | 4 | 170,000 |

TABLE 1-continued

Purification of BTC-GF

| Purification Step | Total Protein, mg | Total Activity, U | Specific Activity, U/mg | Activity Recovery | Purification Fold |
|---|---|---|---|---|---|

Values were based on processing of 10 liters of conditioned medium.
Biological activity was measured by DNA Synthesis in mouse 3T3 cells.
One unit of growth factor activity is defined as the amount of growth factor needed to stimulate half-maximal incorporation of [methyl-$^3$H]thymidine into DNA.
Protein mass was estimated by using $A_{280}$ = 1.0 for a 1 mg/ml solution.
*Protein mass was estimated by the intensity of silver stain compared to that of the protein standards and amino acid analysis.

REFERENCE EXAMPLE 1

Primary cultures of BTC-3 pancreatic beta tumor cells (ATCC Accession No. CRL 10585) were prepared in Dulbecco's modified Eagles medium (DMEM) containing 10% calf serum. These cultures were plated on 162 cm$^2$ cell flasks (Costar Cat #3150) and incubated in a 37° C. humidified $CO_2$ incubator. These cells were used as a source for seeding into 900 cm$^2$-growth-area roller bottles (Costar Cat #3901) containing 125 ml of DMEM with 5% calf serum. The bottles were gassed with 95% air/5% $CO_2$ and rotated on a Cell Production Roller Apparatus (Bellco) at 0.5 rpm in a 37° C. incubator. After 4 days the medium in each bottle was replaced with serum-free medium. The medium was harvested and replaced with fresh medium after incubation for 48–72 hours. Six liters of conditioned medium were collected weekly as the starting materials for the purification of growth factors.

REFERENCE EXAMPLE 2

Method for the Purification of mouse BTC-GF from BTC-3 Cells

Step 1. Concentration.

Ten liters of serum free beta tumor cell conditioned medium were concentrated to 500 ml at 4° C. with an Amicon hollow fiber concentrator using a filter of 10,000 molecular weight cutoff. The concentrated medium was subsequently equilibrated to 50 mM NaCl, 10 mM Tris, pH 7 by continuous dialysis.

Step 2. BioRex 70 Chromatography.

The concentrated medium was applied to a BioRex column (200 ml bed volume) equilibrated with 10 mM Tris, pH 7 at 4° C. The column was rinsed with 400 ml of the same buffer and the biological activity was then eluted with a NaCl gradient from 400 ml of 0M to 400 ml of 0.6M at a flow rate of 60 ml/hour (FIG. 1).

Step 3. Phenyl-Sepharose Chromatography.

Figure 2:
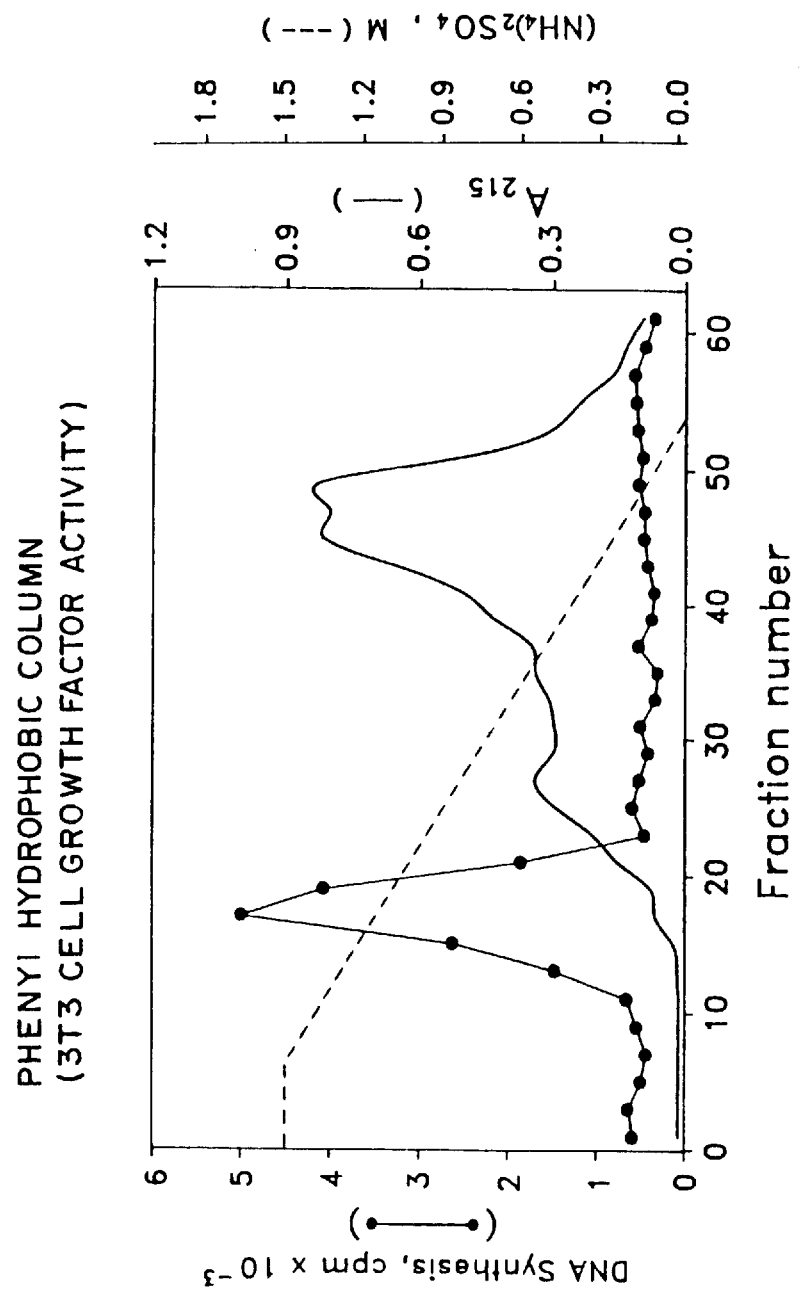
FIG. 2 illustrates the 3T3 cell growth factor activity of pooled active fractions from FIG. 1 when passed through a phenyl-Sepharose column.

The active fractions from BioRex column were pooled, boiled for 5 minutes and clarified by centrifugation (10,000× g, 20 minutes). The clear supernatant solution was brought to 1.5M $(NH_4)_2SO_4$ and applied to a phenyl-Sepharose column (25 ml bed volume) equilibrated at 1.5M $(NH_4)_2SO_4$, 10 mM potassium phosphate buffer, pH 7 at 4° C. The column was rinsed with 100 ml of equilibration buffer and the biological activity was subsequently eluted with a $(NH_4)_2SO_4$ gradient from 170 ml of 1.5M to 170 ml of 0M in 10 mM phosphate buffer at pH 7 at a flow rate of 30 ml/hour (FIG. 2).

Step 4. FPLC Heparin Affinity Chromatography.

Figure 3:
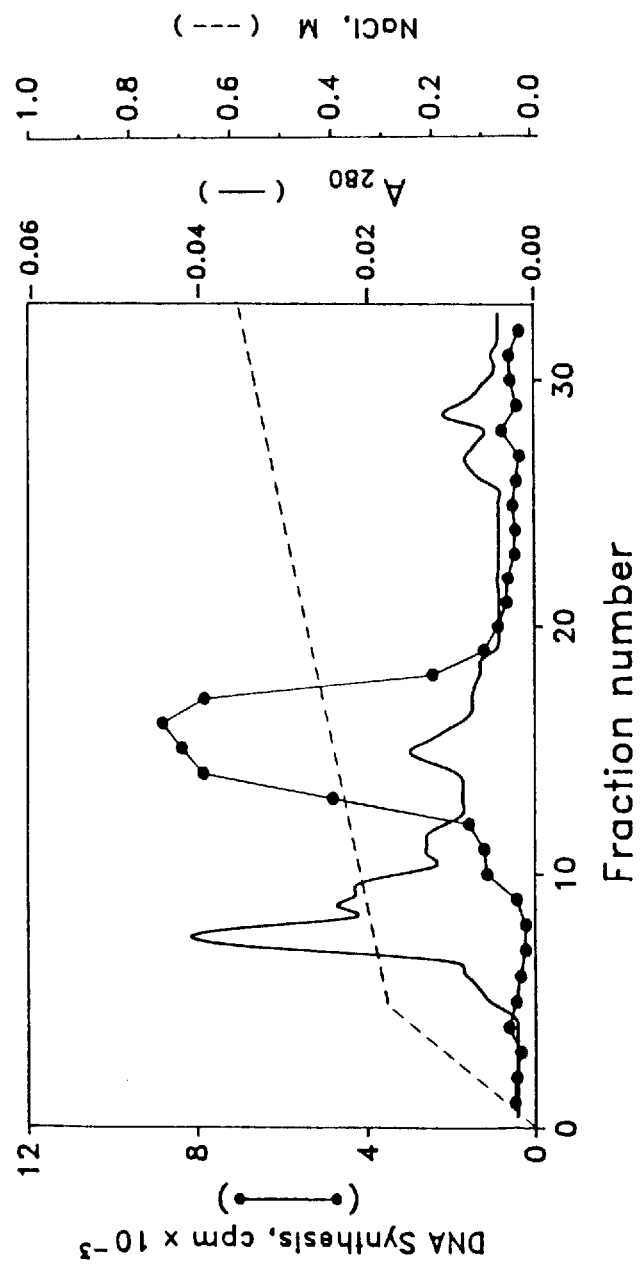
FIG. 3 illustrates the 3T3 cell growth factor activity of the pooled active fractions from the phenyl-Sepharose column when passed through an FPLC heparin affinity column.

The active fractions from phenyl-Sepharose column were pooled, dialyzed and applied to TSK-GEL Heparin 5PW glass column (7.5 cm×8 mm inner diameter) equilibrated with 10 mM Tris, pH 7 at room temperature. The column was rinsed with 10 ml of the same buffer and the biological activity was eluted with NaCl gradient from 0 to 0.3M followed by another NaCl gradient from 0.3 to 0.6M at a flow rate of 1 ml/min/fraction (FIG. 3).

Step 5. HPLC C4 Reverse Phase Chromatography.

Figure 4:
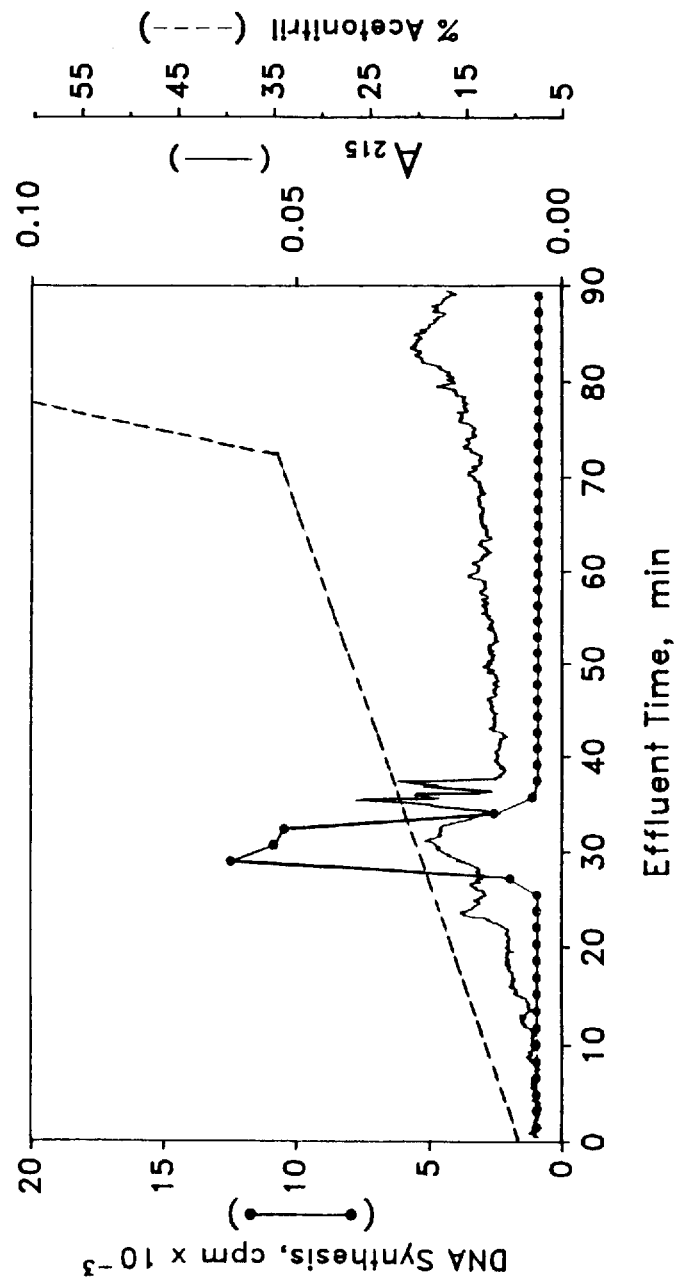
FIG. 4 illustrates the 3T3 cell growth factor activity of the pooled active fractions from the heparin affinity column when passed through an HPLC C4 reverse phase column.
Figure 5:
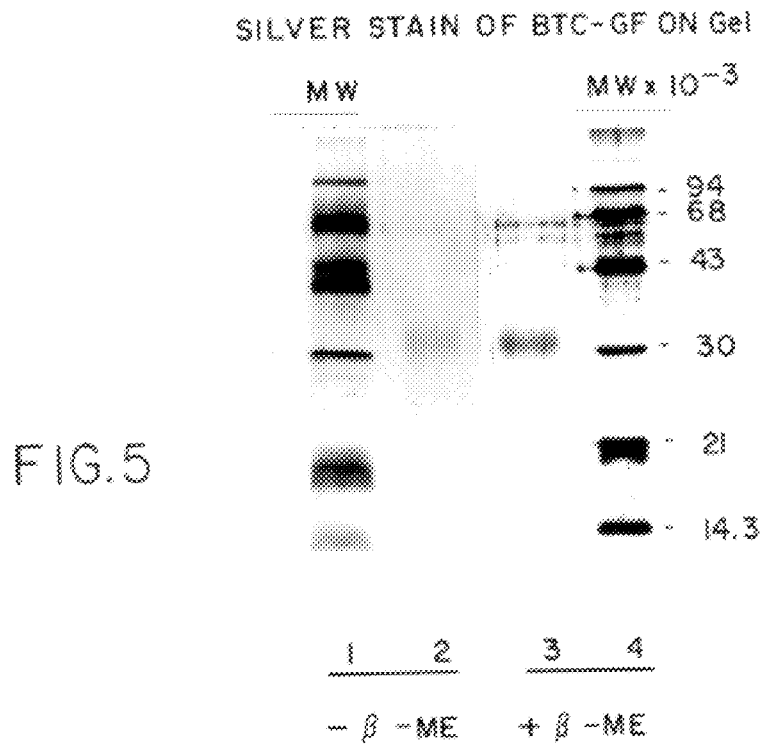
FIG. 5 is a silver stain of mouse BTC-GF on a gel from the pooled active fractions obtained by repeating the HPLC C4 reverse phase column purification.

The active fractions from Heparin column were pooled and injected directly into a HPLC reverse phase C4 column equilibrated with 10% acetonitrile in 0.1% TFA at room temperature. The column was rinsed with 20 ml of the same solution and the biological activity was eluted with a gradient of acetonitrile from 10 to 35% at a flow rate of 2 ml/min and fractions of 1.5 ml were collected (FIG. 4). This step was repeated once in order to obtain a silver-stained single band protein on SDS PAGE (FIG. 5).

A summary of the result of purification is shown in Table 1.

REFERENCE EXAMPLE 3

Mitogenic Activity of Mouse BTC-GF on Smooth Muscle Cell

Figure 6:
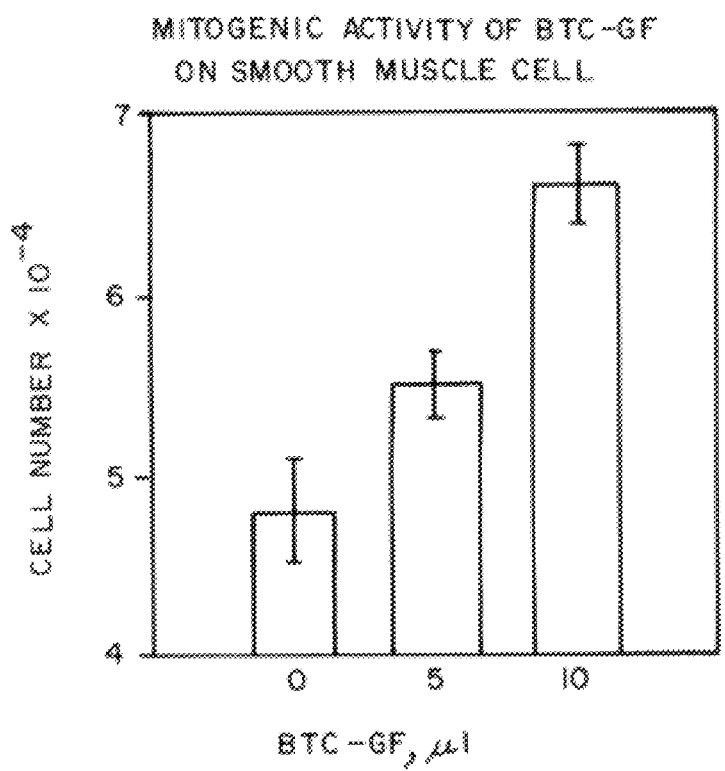
FIG. 6 illustrates the mitogenic activity of mouse BTC-GF on bovine smooth muscle cell.

The purified BTC-GF of Reference Example 2 stimulated the proliferation of bovine aortic smooth muscle cell (SMC) (FIG. 6). The mitogenic activity of mouse BTC-GF was tested on SMC cultured in DMEM containing 1% calf serum. Four days after the test samples were added to the cultures, the cells were trypsinized and the numbers of cells in each well of the 24 well plates were counted with a Coulter Counter.

The protein produced by the above-exampled purification protocol has the following characteristics: mouse BTC-GF is a polypeptide having N-terminal amino acid sequence: Asp-Gly-Xaa-Thr-Xaa-Arg-Thr-Pro-Glu-Xaa-Asn-Gly-Ser-Leu-Xaa-Xaa-Ala-Pro-Xaa-Xaa-Xaa-Xaa-Xaa-Xaa (SEQ ID NO:2). It has a molecular weight of 32,000 as determined by SDS polyacrylamide gel electrophoresis. Its mitogenic activity is not inactivated by exposure to high temperature (100° C., 5 minutes), sulfhydryl reducing agent (10 mM dithiothreitol) or acidic condition (pH 2.2).

REFERENCE EXAMPLE 4

BTC-JC10 was maintained in Dulbecco's modified Eagle medium (DMEM) supplemented with 10% calf serum. For the generation of conditioned medium, 10$^4$ cells/ml of BTC-JC10 cells were grown in suspension in DMEM/F12 (1:1) medium supplemented with 2 mM glutamine, 100 U/ml penicillin, and 100 μg/ml streptomycin; 0.5% insulin, transferin and selenium (ITS, Sigma); and 0.1% polyethylene glycol 400, in a 8-liter spinner flask (Belco glass). The conditioned medium was collected when the cell density reached 2×10 10$^5$ cells/ml.

Mouse BTC-GF was purified from BTC-JC10 conditioned medium by the methods similar to those for the purification of mouse BTC-GF from BTC-3 cells. The partial N-terminal amino acid sequence of mouse BTC-GF purified from BTC-JC10 cells is depicted in SEQ ID NO: 1.

As can be seen from FIG. 7, the N-terminal amino acid sequence of mouse BTC-GF from BTC-3 cells and BTC-JC10 cells appears to be identical, indicating that the two proteins are the same from both types of cells.

EXAMPLE 1

(Cloning of the mouse BTC-GF cDNA)

Mouse BTC-GF is a polypeptide having an internal amino acid sequence:

—His—Tyr—Cys—Ile—His—Gly—Arg—Cys—Arg—Phe—Val—Val—Asp—Glu—Gln—Thr—Pro—Ser—Cys—Ile—Cys—Glu—Lys—
(which corresponds to amino acid Sequence Nos. 12–34 of SEQ ID NO:3).

Based on the partial amino acid sequences of mouse BTC-GF determined in REFERENCE EXAMPLE 3 and 4 (FIG. 7 and 8), 4 oligo nucleotides corresponding to 4 amino acid sequences covering N terminal amino acids Nos. 7–12 of SEQ ID NO:1 and SEQ ID NO:2 (Thr-Pro-Glu-Thr-Asn-Gly), Nos. 17–23 of SEQ ID NO:1 (Ala-Pro-Gly-Glu-Glu-Arg-Thr) and internal amino acids Nos. 1–6 12–18 of SEQ ID NO:3 of FIG. 8 (His-Tyr-Cys-Ile-His-Gly), Nos. 12–17 of FIG. 8 (Val-Asp-Glu-Gln-Thr-Pro which corresponds to amino acid sequence nos. 23–28 of SEQ ID NO:3) were chemically synthesized. In the following primers, I (Inosine) was used at certain third positions at degenerated codons. Thus, the base sequences of oligonucleotides synthesized were primer 1: 5' ACI CCI GA A/G ACN AA T/C GG 3' (SEQ ID NO:6)
primer 2: 5' GCI CCI GGI GA A/G GA A/G C/A GN AC 3'
(SEQ ID NO:7)
primer 3: 5' CC A/G TG T/G/A AT A/G CA A/G TA A/G TG 3' and
(antisense) (SEQ ID NO:8)
primer 4: 5' GG NGT T/C TG T/C TC A/G T CNAC 3' (SEQ ID NO:9)
(antisense)
and (N shows A, T, G or C).

Poly(A) RNA was prepared from BTC-JC10 cells using RNA extractions kit (Pharmacia) and mRNA purification kit (Pharmacia). cDNA was synthesized with the Poly(A) RNA and random hexanucleotide primer (cDNA synthesis system plus, Amersham) using these cDNAs as templates and 2 oligonucleotides (primer 1 and 4) as primers. The first PCR (polymerase chain reaction) was run (30 cycles at 94° C. for 1 min., at 45° C. for 2 min. and at 72° C. for 2 min.). The 2nd PCR was run (30 cycles at 94° C. for 1 min., at 45° C. for 2 min. and at 72° C. for 2 min.) using the products by first PCR, and primer 2 and 3.

The products (amplified DNA by 2nd PCR) were fractionated by 1.5% agarose gel electrophoresis and the DNA having the size of about 0.1 Kb was eluted from the gel. This DNA was labeled with $^{32}$P by random primming method.

BTC-JC10 cDNAs mentioned above were ligated to λgt10 vector digested with EcoRI and dephosphorylated (Stratagene) and the phage vectors were packaged (GIGAPACK II GOLD, Stratagene) to make a cDNA library. This cDNA library (about 5×10$^6$ clones) was plated with *Escherichia coli* NM514 (Yk$^-$Mk$^-$) and the plaques appeared were transferred on 6 pieces of filters (Hyband N, Amersham) in an amount of about 3×10$^5$ clones per filter and lysed with 0.5N NaOH, and phage DNAs exposed and denatured were immobilized on the filters.

The labeled DNA was hybridized as a probe with the filters. The hybridization reactions was conducted in 10 ml of a 100 μg/ml of denatured salmon sperm DNA solution containing 10 μCi of probe in 5× SSPE [180 mM NaCl, 10 mM NaH$_2$PO$_4$, 1 mM EDTA (pH 7.4)] and 5× Denhardt's with 0.1% SDS at 65° C. for 16 hours. After reaction the filter were washed with a 0.1% SDS solution in 0.2× SSC two times each at 65° C. for 30 min.

Radioautograms were taken for the washed filters and a positive plaque was searched for by superposing the radioautograms on the plates. In this manner, 7 positive phage clones were obtained from 2×10$^6$ plaques. Then, using the DNAs from these positive clones, and primer 2 and 3, PCR was tried and an expected size of DNA (0.1 Kb) was amplified with only 2 clones. One of them (λgt10TC-3) was shown to have 1.2 Kb of cDNA at EcoRI site. This cDNA was inserted into the EcoRI site of plasmid pUC119 (plasmid pTB1489). The plasmid pTB 1489 was introduced into *Escherichia coli* DHTαF'(Bethesda Research Laboratory, USA) to obtain a transformant *Escherichia coli* DH5αF'/pTB 1489 (IFO 15256). This transformant has been deposited at the Institute for Fermentation, Osaka (IFO), Japan under the deposit number of IFO 15256 as well as in the American Type Culture Collection on Feb. 10, 1992 under ATCC Accession No. 68911.

The base sequence of the cDNA, namely 1.2 Kb of EcoRI DNA fragment, was determined by the dideoxynucleotide synthetic chain termination method [J. Messing et al.: Nucleic Acids Research 9: 309 (1981)]. Based on the results of sequencing, the whole amino acid sequence of mouse BTC-GF could be determined.

The base sequence of the cDNA and the amino acid sequence predicted from said base sequence are shown in FIG. 9 (SEQ ID NO. 4). In FIG. 9, the abbreviation "End" stands for terminator codon and the N terminal amino acid residue (amino acid No. 1 Asp) of mouse BTC-GF was estimated from that of FIG. 7.

The 30 amino acid residues upstream from said N terminal amino acid residue presumably constitute a signal peptide. The arrow shows the site of processing between signal peptide and mature mouse BTC-GF.

EXAMPLE 2

(Construction of Mouse BTC-GF cDNA Expression Plasmid for Mammalian Cells)

A 1.2-kb EcoRI fragment containing the BTC-GF cDNA was isolated from the plasmid pTB1489, obtained in Example 1. The expression plasmid pTB701 [J. Biol. Chem. 263, 6927 (1988)] was cleaved with EcoRI and then treated with calf intestine phosphatase. The resulting plasmid was ligated to the above 1.2-kb EcoRI fragment containing BTC-GF cDNA. The ligation mixture was used for the transformation of *E. coli* DH1 (Molecular Cloning; A Laboratory Manual, Cold Spring Harbor Laboratory, p.505, 1982). A plasmid was isolated from the resulting ampicillin-resistant transformants, and this plasmid was named pTB1491.

EXAMPLE 3

(Expression of BTC-GF cDNA in mammalian cells)

Monkey COS7 cells were plated (3×10$^5$ cells/dish) and cultured in Dulbecco's modified Eagle's medium (DMEM, Flow Labs.) containing 10% fetal calf serum. Ten micrograms of the expression plasmid pTB1491 (Example 2) and pTB1495 (having the same construct to pTB1491 except the inverted orientation of BTC-GF cDNA) were introduced into COS7 cells using the calcium phosphate method [Graham et al., Virology 52, 456 (1973)]. On the next day the culture medium was changed to DMEM containing 0.5% fatal calf serum, followed by cultivation for 2 days. The conditioned medium was collected and assayed for the stimulation of DNA synthesis by $^3$H-thymidine incorporation into resting BALB/c 3T3 A31-714 clone 4: Int. J. Cancer 12, 463 (1973) as described [Mol. Cell. Biol. 8, 588 (1988)] The results are shown below in Table 2.

TABLE 2

| DNA transfected | Sample dilution | $^3$H-Tdr incorporation (cpm) |
|---|---|---|
| pTB1491 | 1/250 | 42,155 |
|  | 1/1250 | 30,023 |
| pTB1495 | 1/250 | 1,168 |
| — | — | 2,030 |

EXAMPLE 4

(Cloning of human BTC-GF cDNA)

Poly (A) RNA was prepared from a human breast adenocarcinoma cell line MCF7 (ATCC HTB22, ATCC Catalogue of Cell Lines and Hybridomas, Sixth Edition, 1988) using RNA extraction kit (Pharmacia) and mRNA purification kit (Pharmacia). cDNAs were synthesized with poly(A) RNA and random hexanucleotide primer (cDNA synthesis system plus, Amersham). These cDNAs were integrated into BstXI site of plasmid pME18S (medical Immunology 20, 27 (1990) using BstXI adapter and transformed Escherichia coli DH5αF' to make a cDNA library.

This cDNA library was plated on 10 pieces of nitrocellulose filter (Millipore's HATF filter) in an amount of about $5 \times 10^4$ clones per filter. Using these filter as master filters, replica filters were prepared corresponding to master filter. Escherichia coli cells on these replica filters were lysed with 0.5N NaOH and plasmid DNAs exposed and denatured were immobilized on the filters (Grunstein, M. & Hogness, D. S. : Proc. Natl. Acad. Sci. USA, 72 3961 (1975)).

The plasmid pTB 1489, obtained in Example 1, was digested with EcoRI and NhaI, and 0.73 kb DNA fragment coding for a mouse BTC-GF was isolated. This DNA fragment was labeled with $^{32}$P by the nick translation method (Rigby, P. W. J. et al.: Journal of Molecular Biology, 113, 237 (1977)).

The thus-labeled DNA was hybridized as a probe with the replica filters. The hybridization reaction was conducted in 10 ml of 100 µl/ml denatured salmon sperm DNA solution containing 10 µCi of probe in 5x SSPE (180 mM NaCl, 10 mM NaH$_2$PO$_4$, 1 mM EDTA (pH 7.4)) and 5x Denhardt's with 0.1% SDS at 60° C. for 16 hours. After reaction, the filters were washed with 0.1% SDS solution in 2x SSC (0.15M NaCl, 0.015M sodium citrate) two times each at room temperature for 30 minutes and then two times each at 60° C. for 30 minutes (T. Maniatis et al.: "Molecular Cloning", Cold Spring Harbor Laboratory, page 309 (1982)).

Radioautograms were taken for the washed filters. A bacterial colony was searched for by superposing the radioautograms of replica filters. In this manner, a strain, Escherichia coli K12 DH1/pTB1499, capable of reacting with the probe was obtained from among $5 \times 10^5$ colonies.

The plasmid DNA, pTB1499, was extracted from the strain obtained above by the alkaline extraction method (Birnboim, H. C. & Doly, J., : Nucleic Acids Res. 1: 1513 (1979)) and purified. The cDNA portion of the plasmid DNA was excised by using the restriction enzyme BstXI (Takara Shuzo) and fractionated by agarose gel electrophoresis.

Then, the base sequence of the cDNA portion mentioned above was determined by the dideoxynucleotide synthetic chain termination method (J. Messing et al. : Nucleic Acids Res., 9 309 (1981)).

Based on the results of sequencing, the whole amino acid sequence of human BTC-GF was able to be determined.

The base sequence of the cDNA and the amino acid sequence predicted from said base sequence are shown in FIG. 10. The arrow shows the site of processing between signal peptide and mature human BTC-GF.

The plasmid pTB1499 was introduced into Escherichia coli DH5α (Bethesda Research Laboratory, USA) to obtain a transformant Escherichia coli DH5α/pTB1499. This transformant has been deposited at the IFO on Jan. 14, 1992 under the deposition number of IFO 15257 as well as in the American Type Culture Collection on Feb. 10, 1992 under ATCC Accession No. 68910.

EXAMPLE 5

(Construction of human BTC-GF cDNA expression plasmid for mammalian cells)

Figure 11:
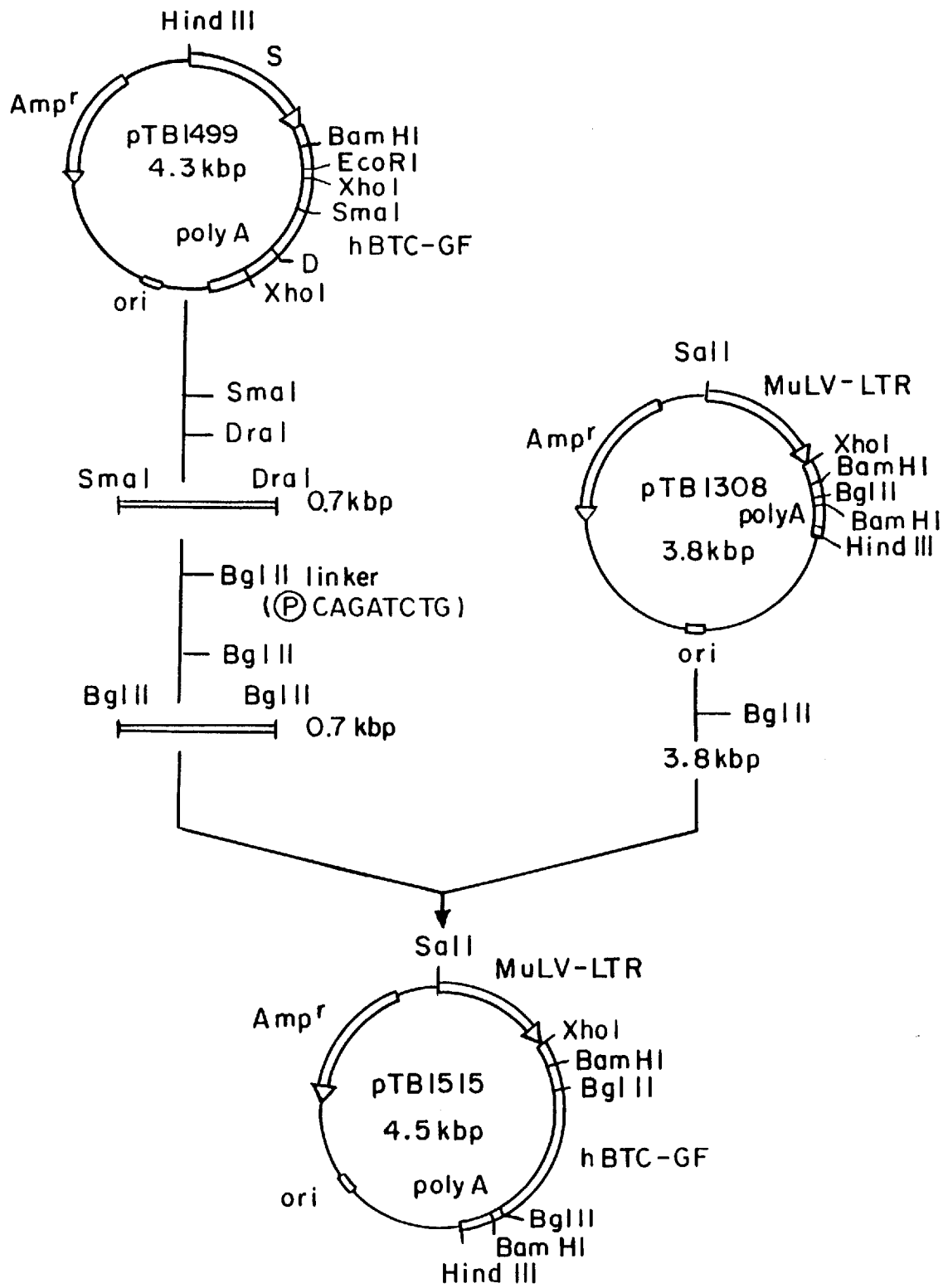
FIG. 11 shows the construction scheme of plasmid pTB 1515.
Figure 12:
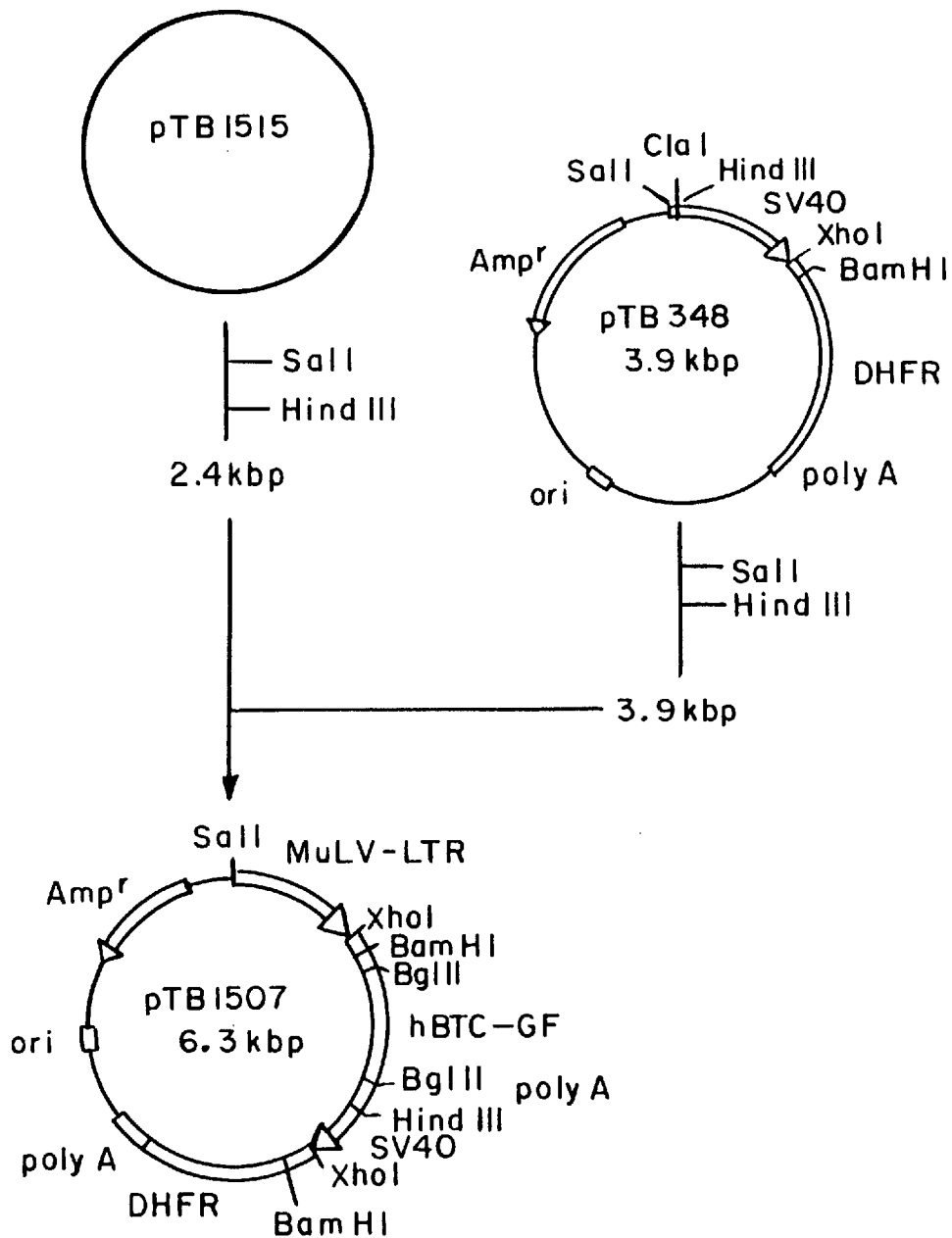
FIG. 12 shows the construction scheme of plasmid pTB 1507.

A 0.7 kb SmaI-DraI fragment containing the human BTC-GF cDNA was isolated from the plasmid pTB1499 (Example 4). The BglII linker (5'CAGATCTG 3') was ligated to the flush ends of this fragment using T4 DNA ligase. After digesting with BglII, the 0.7 kb fragment containing human BTC-GF cDNA was inserted into the BglII site of an expression plasmid pTB1308 by ligation with T4 DNA ligase, which was prepared from pTB399 [Cell Struct. Funct. 12, 205 (1987)] by removing the IL-2 cDNA region (FIG. 11). The resulting plasmid (pTB1515) was then cleaved with SalI and HindIII. The 2.4 kb fragment containing a MuLV LTR and a human BTC-GF cDNA was isolated and introduced between SalI-HindIII sites of pTB348 [Cell Struct. Funct. 12, 205 (1987)] having the SV40 early-region promoter and hamster DHFR cDNA. The resulting plasmid was named pTB1507 (FIG. 12).

EXAMPLE 6

(Construction of human BTC-GF cDNA expression plasmid of E. coli)

A 0.6 kb EcoRI-BamHI fragment encoding mature human BTC-GF (1–147 amino acid residues) was isolated from the plasmid pTB1515 (Example 5). After ligating synthetic adapters having ATG translational initiator codon (a: 5'TATGGATGGG 3' (SEQ ID NO:12), b; 5'AATTC-CCATCCA 3' (SEQ ID NO:13)) to the EcoRI site of the above 0.6 kb fragment, the resulting 0.6 kb NdeI-BamHI fragment was inserted into the plasmid pET-3c carrying T7 promoter [Gene 56, 125 (1987)] to construct the plasmid pTB1505.

Figure 13:
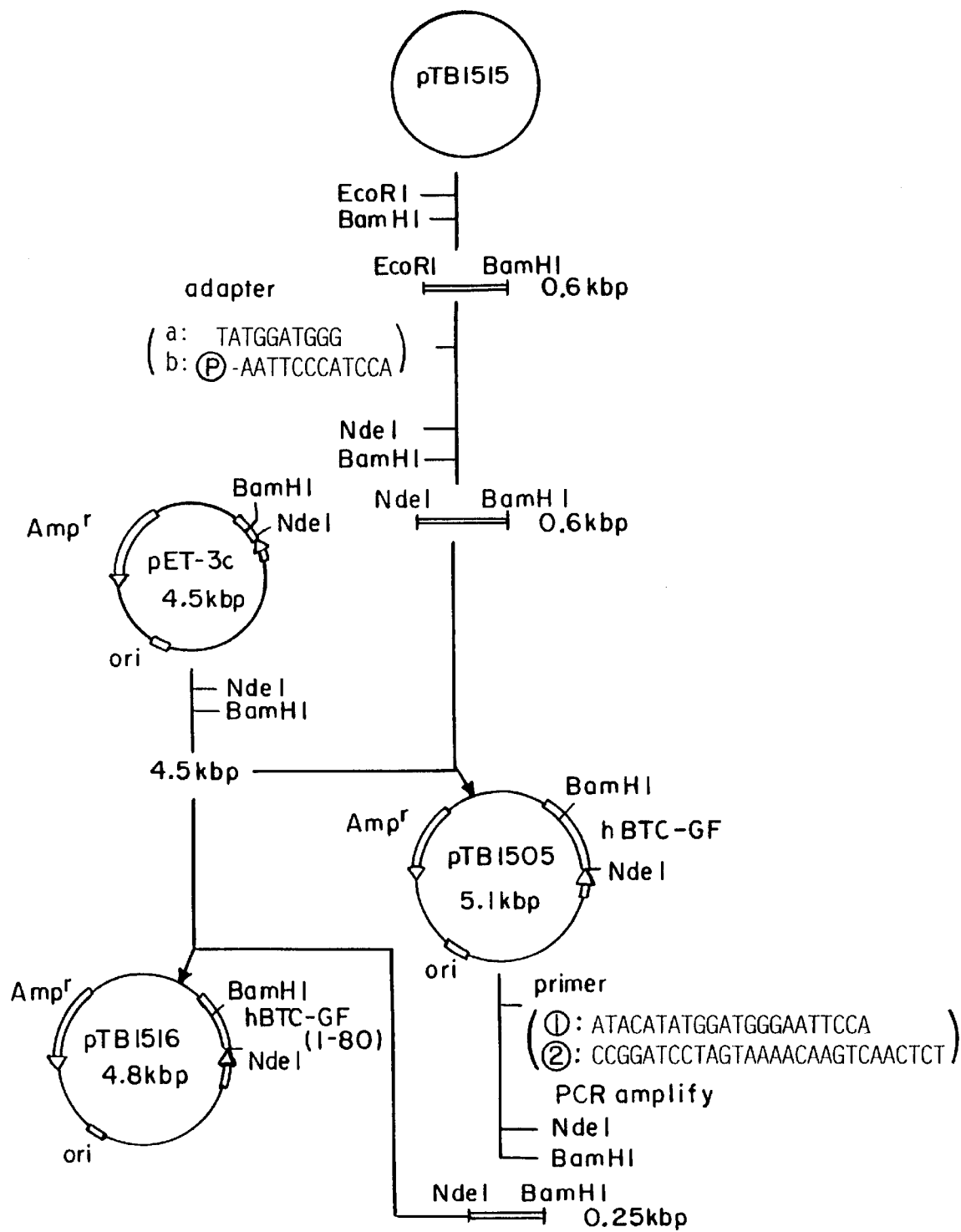
FIG. 13 shows the construction scheme of plasmid pTB 1516.

To obtain a DNA fragment encoding 80 amino acid residues of human BTC-GF [1(Asp)–80 (Tyr) residues of FIG. 10 (SEQ ID NO:17)], PCR was run using the plasmid pTB1505 as a template and 2 oligonucleotides (1; 5'ATA- CATATGGATGGGAATTCCA 3' (SEQ ID NO:10), 2; 5'CCGGATCCTAGTAAAACAAGTCAACTCT 3' (SEQ ID NO:11)) as primers. The products were digested with NdeI and BamHI, fractionated by 2.0% agarose gel electrophoresis, and the expected 0.25 kb DNA fragment was isolated. This 0.25 kb NdeI-BamHI fragment was inserted downstream of the T7 promoter of pET-3c by ligating with T4 DNA ligase to give plasmid pTB1516 (FIG. 13).

EXAMPLE 7

(Expression of human BTC-GF cDNA in mammalian cells)

Monkey COS7 cells were plated ($3 \times 10^5$ cells/dish) and cultured in Dulbecco's modified Eagle medium (DMEM, Flow Labs.) containing 10% fetal calf serum. Ten micrograms of the expression plasmid pTB1499 (Example 4) and pTB1507 (Example 5) were introduced into COS7 cells using the calcium phosphate method [Virology 52 456 (1973)], respectively. On the next day the culture medium was changed to DMEM containing 0.5% fetal calf serum, followed by cultivation for 2 days. The conditioned medium was collected and assayed for the stimulation of DNA synthesis by $^3$H-thymidine incorporation into resting BALB/c 3T3 A31-714 clone 4[Int. J. Cancer 12, 463 (1973)] as described [Mol. Cell. Biol. 8, 588 (1988)]. The results are shown in Table 3.

TABLE 3

| DNA transfected | Sample dilution | $^3$H-Tdr incorporation (cpm) |
|---|---|---|
| pTB1499 | 1/125 | 15,002 |
|  | 1/625 | 5,120 |
| pTB1507 | 1/625 | 19,898 |
|  | 1/3125 | 16,344 |
| — | 1/125 | 1,008 |

EXAMPLE 8

(Expression of human BTC-GF cDNA in *E. coli*)

*Escherichia coli* MM294 was lysogenized with lambda phage DE3 (Studier, supra), in which the RNA polymerase gene of T7 phage had been recombined. Thereafter, the plasmid pLysS was introduced into *E. coli* MM294(DE3) to give *E. coli* MM294(DE3)/pLysS. To this strain, plasmid pTB1516 was introduced, whereby *E. coli* MM294(DE3)/pLysS, pTB1516 was obtained. The transformant was cultivated in 20 ml of L-broth containing 100 µg/ml of ampicillin and 10 µg/ml of chloramphenicol at 37° C. When the Klett value was about 180, isopropyl beta-D-thiogalactoside (IPTG) was added to the medium to 0.4 mM as the final concentration, and the cultivation was continued for 4 hours. The bacterial cells were collected by centrifugation, and suspended in 0.5 ml of buffer containing 20 mM Tris-Hcl (pH7.4), 10 mM EDTA, 0.5M NaCl, 10% sucrose and 0.25 mM PMSF and then to the suspension egg white lysozyme was added at a concentration of 0.5 mg/ml. After keeping it in an ice-bath for one hour, the mixture was incubated at 37° C. for 5 minutes, subjected to centrifugation (SORVALL, 15000 rpm for 30 minutes at 4° C.) to give a supernatant.

The bacterial extract was assayed for the stimulation of DNA synthesis by $^3$H-thymidine incorporation into resting BALB/c 3T3 cells as described in Example 7. The results are shown in Table 4.

TABLE 4

| Transformant | Sample-dilution | $^3$H-Tdr incorporation (cpm) |
|---|---|---|
| *E. coli* MM294(DE3)/pLysS, pTB1516 | 1/78125 | 20,232 |
|  | 1/390625 | 13,169 |
| *E. coli* MM294(DE3)/pLysS, pET-3c | 1/3125 | 805 |

The transformant *Escherichia coli* MM294(DE3)/pLysS, pTB1516 has been deposited at the IFO on Apr. 16, 1992 under the deposition number of IFO 15282, as well as in the Fermentation Research Institute, Agency of Industrial Science and Technology, Ministry of International Trade and Industry, Japan (FRI) on Apr. 21, 1992 under Accession No. FERM BP-3836.

EXAMPLE 9

(Establishment of CHO cell strains producing hBTC.)

Expression plasmid pTB1507 (Example 5) was introduced into CHO dhfr⁻ cells [Urlaub et al., Proc. Natl. Acad. Sci. USA 77, 4216 (1980)] by the calcium phosphate method. After two days, the medium was exchanged for a selection medium (DMEM containing 10% dialyzed fetal calf serum and 35 µg/ml proline), and cultivation was continued to obtain DHFR⁺ cells. These CHO DHFR⁺ cells were cloned by the limiting dilution method and 60 clones were established. Cells of each clone were grown to reach 80% confluent in a 24 well plate and the medium was changed to 0.5 ml of DMEM/Ham's F12 (1:1) containing 0.5% fetal calf serum and 0.1 µg/ml insulin. After cultivation for 2 days, the conditioned medium was collected and assayed for the mitogenic activity of hBTC as described in Example 3. The conditioned medium of 31 clones out of 60 showed mitogenic activity to mouse 3T3 cells. The mitogenic activity was 0.1 to 5.0 ng/ml, calculating the activity by determining the dilution of factor required to give 50% of the maximal stimulation and indicating as the weight of the standard, mouse EGF.

EXAMPLE 10

(Establishment of A9 cell strains producing hBTC.)

Mouse A9 cells (ATCC CCL 1.4) were transfected with expression plasmids, pTB1515 (Example 5) containing hBTC cDNA and p4aA8 [Jolly, D. J. et al., Proc. Natl. Acad. Sci. USA, 80, 477 (1983)] containing human HPRT gene simultaneously by the calcium phosphate method. The cells were grown in DMEM supplemented 10% fetal calf serum for 2 days, and then cultured in HAT medium [Littlefield, J. W., Science 145, 709 (1964)] for selection. HPRT⁺ cells grew in HAT medium and clones were isolated by the limiting dilution method. The cells ($10^5$ per well of a 24 well plate) of each clone were plated and cultured for 2 days in a growth medium and then cultured in 0.5 ml of DMEM containing 0.5% fetal calf serum for 2 days. The level of hBTC secreted into the culture medium of $10^6$ cells was examined by the mitogenic activity to mouse 3T3 cells as described in Example 3. The results of several clones are shown below in Table 5.

TABLE 5

| Clone | Activity (ng/ml mouse EGF equivalent) |
|---|---|
| A9/1515-4 | 43 |
| A9/1515-14 | 566 |
| A9/1515-17 | 208 |
| A9/1515-34 | 258 |
| A9/1515-63 | 94 |

The clone A9/1515-14 has been deposited at the IFO on Dec. 28, 1992 under the deposition number of IFO 50389, as well as in the FRI under Accession No. FERM BP-4159 on Jan. 13, 1993.

EXAMPLE 11

(Purification of human BTC-GF produced by a transformed COS7 cell)

Figure 14:
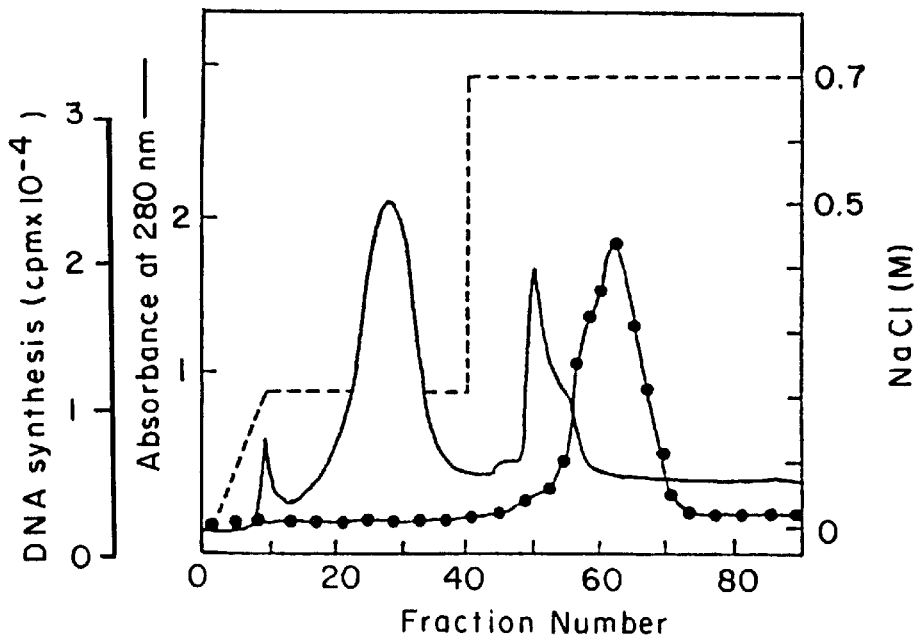
FIG. 14 shows the results of S-Sepharose column chromatography obtained in Example 11.

To one liter of supernatant of culture of COS7 cell in which plasmid pTB1507 has been introduced, 100 ml of 1M potassium phosphate (pH 6.0), 2 ml of 0.5M EDTA, 10 ml of 5% CHAPS (3-[(3-Cholamidopropyl)dimethylammonio]-1-propanesulfonate), and 2 ml of 0.25M PMSF (phenylmethylsulfonyl fluoride) was added, and the solution was applied to S-Sepharose column (1.6×10 cm diameter, Pharmacia) at a flow rate of 2 ml/min. After washing the column with 100 ml of buffer (0.1M potassium phosphate (pH 6.0), 1 mM EDTA, 0.05% CHAPS, 0.5 mM PMSF), gradient concentration of 0M to 0.21M of NaCl was poured into the column from 0 to 10 minutes, 0.21M NaCl was 10 to 40 minutes and after 40 minutes a buffer containing 0.7M NaCl to elute a protein. After measuring DNA synthesis-inducing activity for BALB/c3T3 cells of the respective fraction of 2 ml (one minute each), fractions of No. 51–69 were pooled (FIG. 14).

Figure 15:
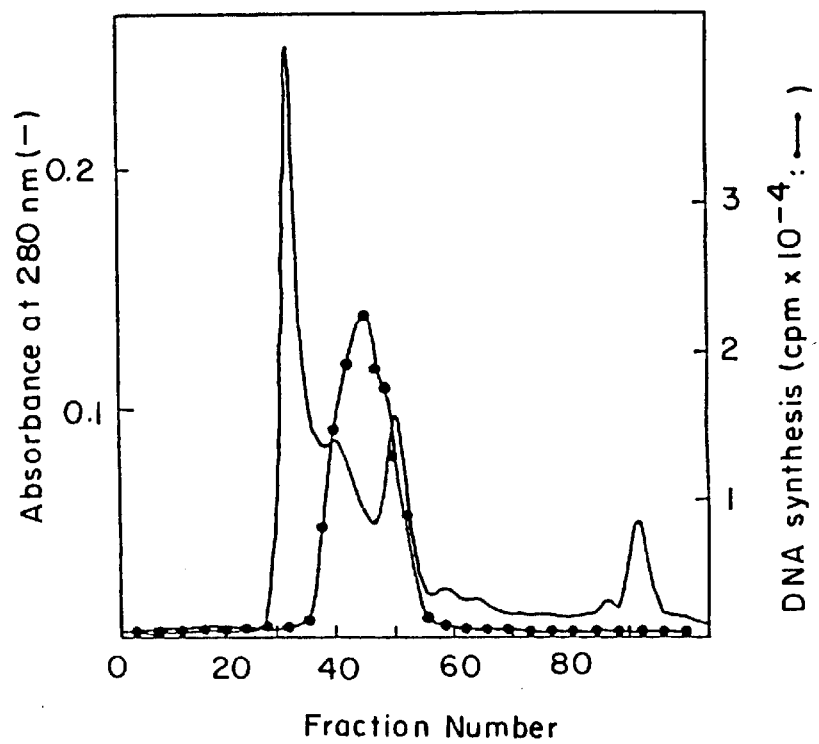
FIG. 15 shows the results of gel-filtration obtained in Example 11.

The pooled fraction of S-Sepharose column was concentrated by ultrafiltration (Centriprep-10, Amicon) and the concentrate was applied to a gel filtration column (Superdex 75 pg, diameter; 1.6×60 cm, Pharmacia), which being already equilibrated by a buffer containing 20 mM Tris (pH7.4) -1 mM EDTA-0.05% CHAPS at a flow rate of 1.2 ml/min. Biological activities were measured in each fraction of 1.2 ml (1 minutes) after 15 minutes of the start, and the fractions 40–50 were pooled (FIG. 15).

Figure 16:
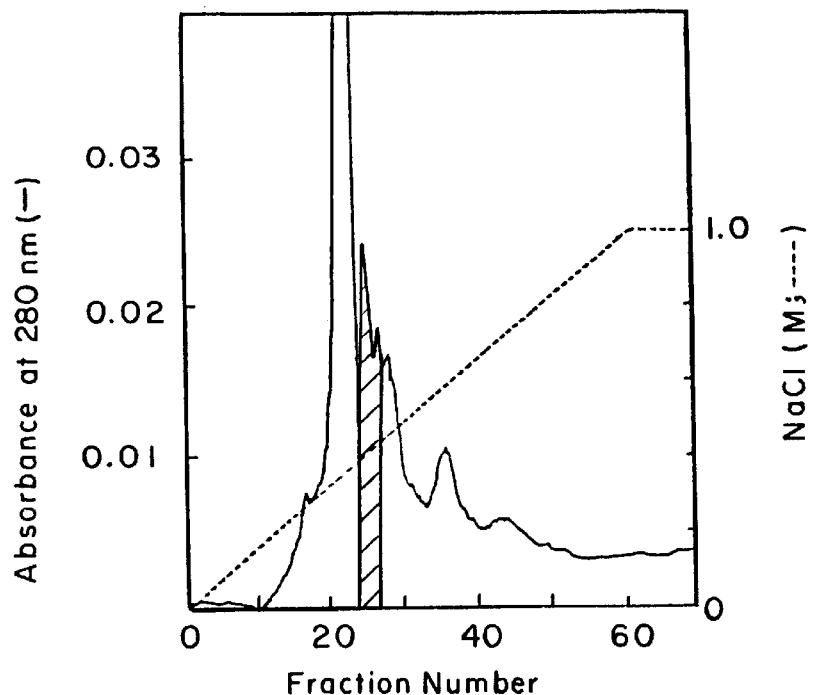
FIG. 16 shows the results of heparin HPLC obtained in Example 11.

The fraction pooled of the gel filtration was applied to a column of heparin HPLC (diameter 0.85×5 cm; Shodex HR-894, Showa-denko). After washing with 20 mM Tris (pH 7.4) -1 mM EDTA-0.05% CHAPS, a gradient elution was carried out by employing 0M to 1M NaCl at a flow rate of 1 ml/min. for 60 minutes, and a fractionated in one minute intervals. The biologically active fractions Nos. 24–28 were pooled (FIG. 16).

Figure 17:
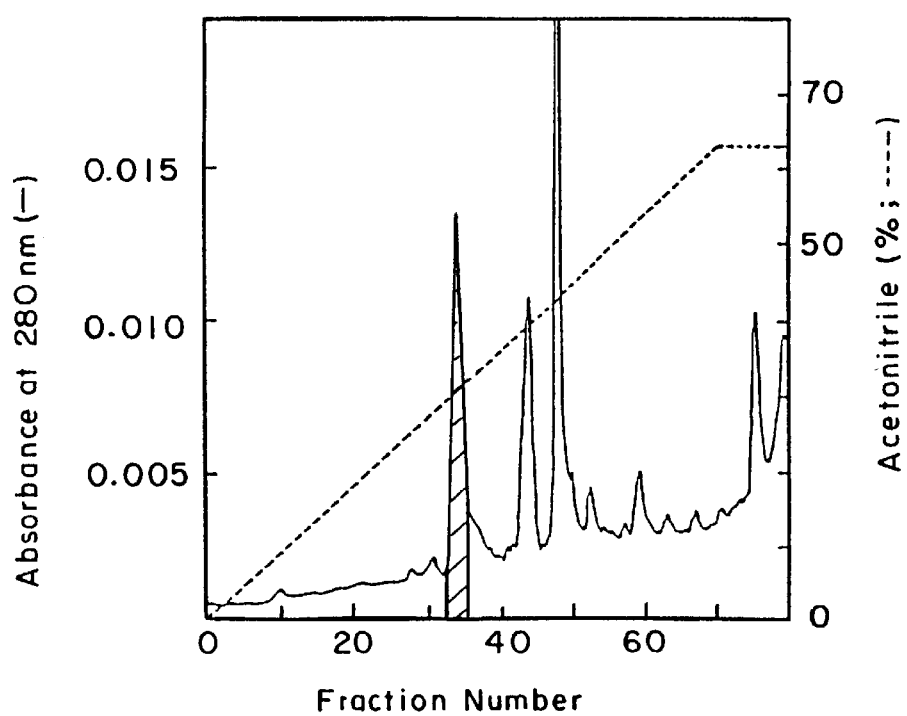
FIG. 17 shows the reverse-phase HPLC obtained in Example 11.

To the fractions pooled of heparin HPLC column was added trifluoro acetic acid (TFA) to be the final concentration of 0.1%, and the mixture was applied to a column of C18 reverse phase HPLC (diameter 0.46×15 cm, Asahipak ODP-5, Asashi Chemical). After washing the column with 0.1% TFA, a gradient elution was carried out with 0% to 63% (v/v) of acetonitrile at a flow rate of 0.5 ml/min. for 70 minutes and the eluted solution was divided into fractionation in each one minute (FIG. 17). The biological activity was confirmed at the peak painted black in FIG. 17.

Figure 18:
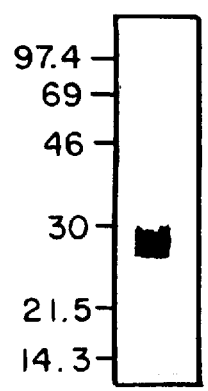
FIG. 18 shows the results of SDS-PAGE/silver staining obtained in Example 11.

SDS-PAGE and silver staining of 20 µl on reverse phase fractionation gave a single band corresponding to molecular weight of 26–30 kD (FIG. 18).

Thus, purified human BTC-GF produced by COS7 cell was obtained.

EXAMPLE 12

(Purification of BTC-GF produced by A9 cell.)

To 3.5 liter of supernatant of culture of A9/1515-14 cell were added 180 ml of 1M potassium phosphate (pH 6.0), 7 ml of 0.5M EDTA, 36 ml of 5% CHAPS, and 7 ml of 0.25M PMSF. The mixture was applied to S-Sepharose column (diameter 2.6×40 cm, Pharmacia).

After washing the column with a buffer (0.1M potassium phosphate (pH 6.0), 1 mM EDTA, and 0.05% CHAPS, 0.5 mM PMSF), a buffer containing the above and 0.7M NaCl was applied at a flow rate 1 ml/min. to elute the protein.

Figure 19:
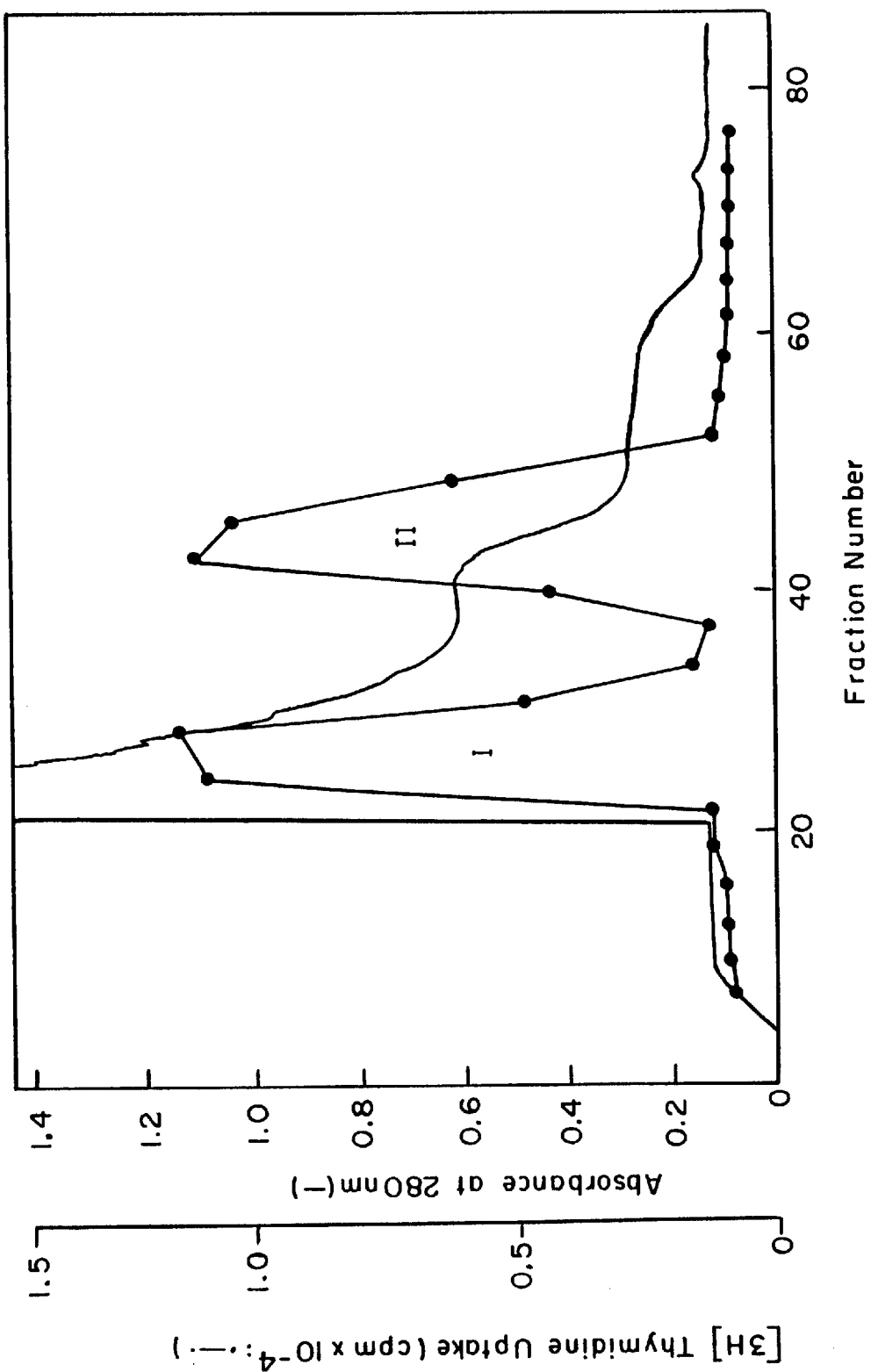
FIG. 19 shows the results of S-Sepharose column chromatography and DNA synthesis inducing activity, obtained in Example 12.

The fractions of 5 ml each were tested on DNA synthesis inducing activity (biological activity) on BALB/c3T3 cell, and the obtained fraction Nos. 23–32 was pooled named as BTC-I and the fraction Nos. 40–49 as BTC-II (FIG. 19).

Figure 20A:
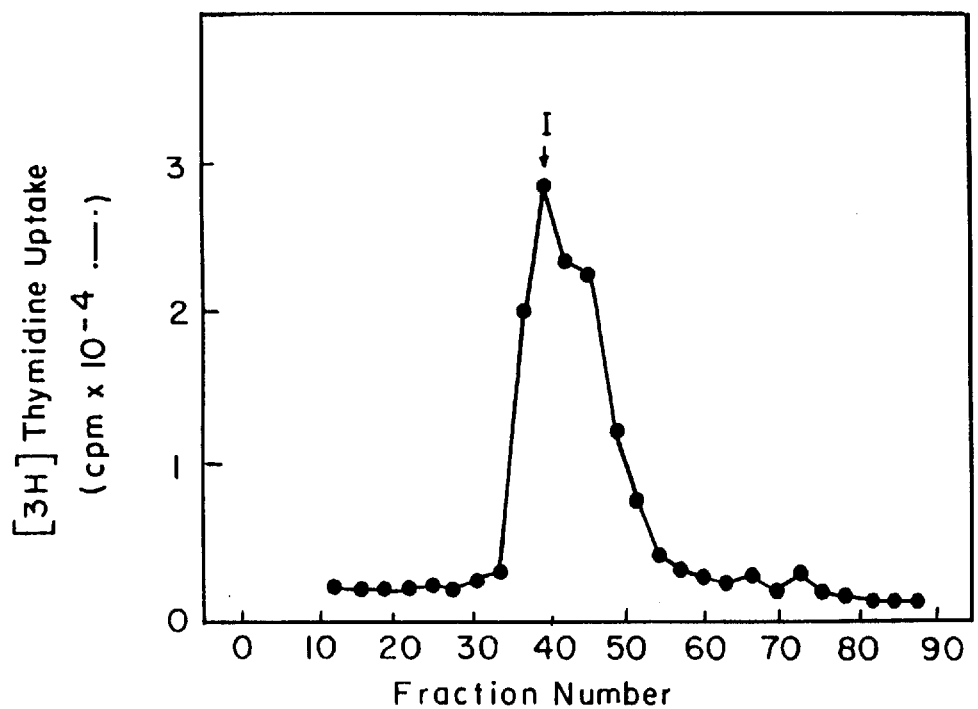
FIGS. 20A and 20B shows the results of gel-filtration obtained in FIG. 12.

After fractionating said BTC-I with 25% and then 80%-saturated ammonium sulfate, the resultant was concentrated by ultrafiltration (Centriprep-10; Amicon) and the concentrate was applied to a column of gel filtration (Superdex 75 pg, diameter 1.6×60 cm, Pharmacia), which being previously equilibrated with 20 mM Tris (pH 7.4), 1 mM EDTA and 0.05% CHAPS, at a flow rate of 1.2 ml/min. From 15 minutes after the starting of the gel filtration, each 1.2 ml portion was collected and high biological activity fractions Nos. 35–41 were pooled (FIG. 20A).

Figure 20B:
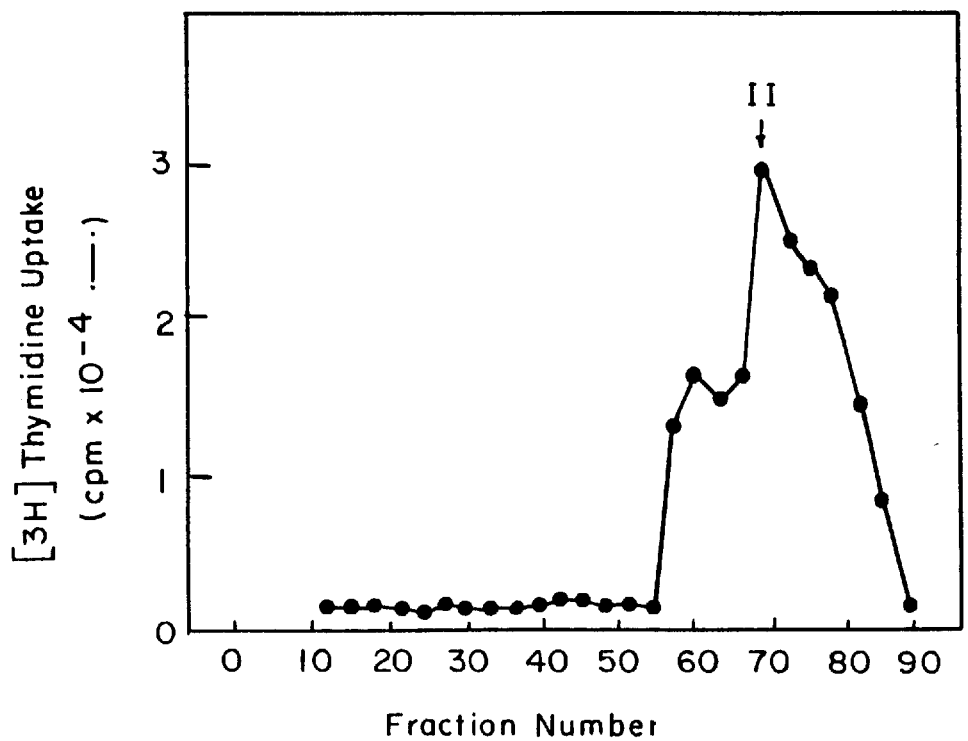

After concentrating, said BTC-II by ultrafiltration (YM2; Amicon) and the concentrate was applied to a column of gel filtration (Superdex 75 pg, diameter 1.6×60 cm, Pharmacia), which being previously equilibrated with 20 mM Tris (pH 7.4), 1 mM EDTA and 0.05% CHAPS, at a flow rate of 1.2 ml/min. From 15 minutes after the starting of the gel filtration each 1.2 ml portion was collected and high biological active fractions Nos. 66–74 were pooled (FIG. 20B).

Figure 21B:
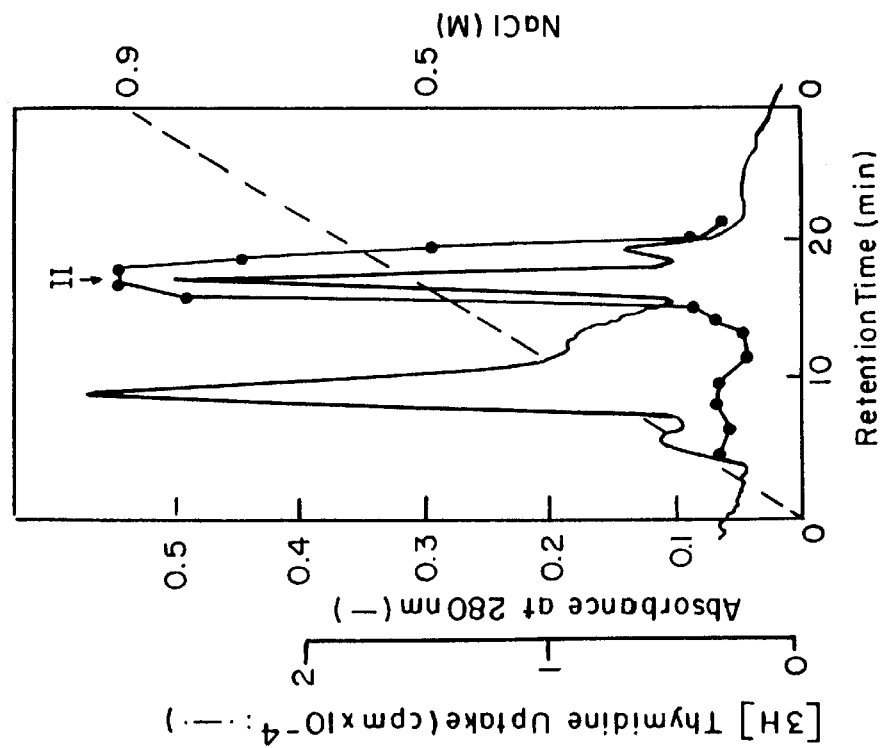
FIGS. 21A and 21B shows the results of heparin HPLC column chromatography obtained in Example 12.
Figure 21A:
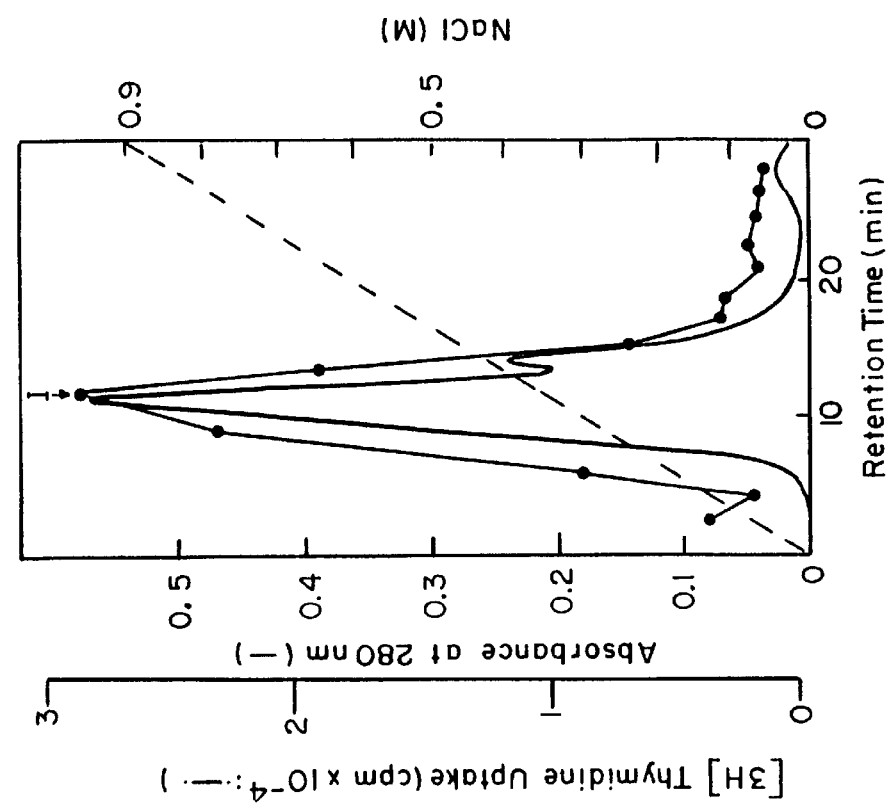

BTC-I fraction collected from the gel filtration column was applied to heparin HPLC column (AF pak HR894, diameter 0.8×5 cm, Showa-denko). After washing the column with 20 mM Tris-HCl (pH 7.4), 1 mM EDTA, 0.05% CHAPS, a gradient elution was carried out with 0–0.9M NaCl at a flow rate 1 ml/min. for 30 minutes and fractionated to 1 ml each. The biologically active fraction Nos. 9–13 were pooled (FIG. 21A).

BTC-II fraction collected from the gel filtration column was applied to heparin HPLC column (AF pak HR894, diameter 0.8×5 cm, Showa-denko). After washing the column with 20 mM Tris-HCl (ph 7.4), 1 mM EDTA, 0.05% CHAPS, a gradient elution was carried out with 0–0.9M NaCl at a flow rate 1 ml/min. for 30 minutes and fractionated to 1 ml each. The biologically active fraction Nos. 16–19 were pooled (FIG. 21B).

Figure 23A:
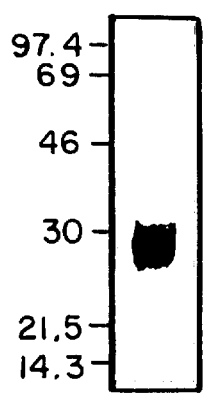
FIG. 23 shows the results of SDS-PAGE/silver staining obtained in Example 12.
Figure 22A:
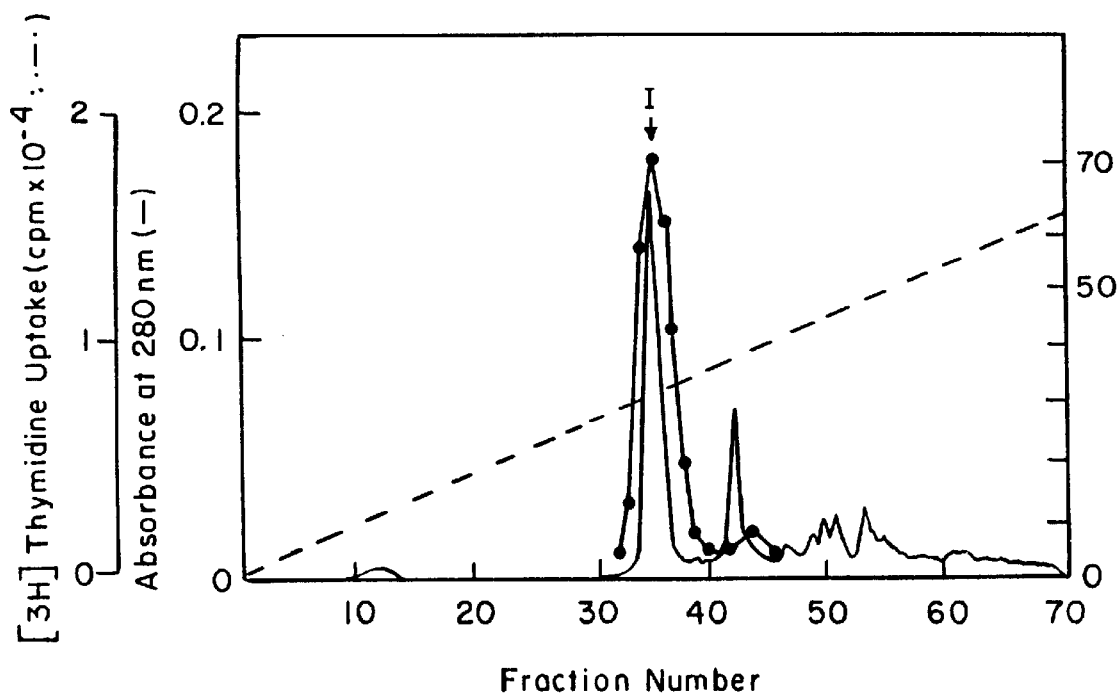
FIGS. 22A and 22B shows the results of reverse-phase HPLC obtained in Example 12.

To the BTC-I fraction collected from the eluate of heparin column was added TFA to a final concentration of 0.1%, and then the mixture was applied to C18 reverse phase HPLC column (Asahipak ODP50, diameter 0.46×15 cm, Asahi Chemical). The eluate thus obtained was applied to a gradient elution of acetonitrile (0–63%) in the presence of 0.1% TFA for 70 minutes and elutions were collected with each 0.5 ml (1 minute) (FIG. 22A). The biological activity was confirmed with the elution peak. From SDS-PAGE/silver staining a single band at the position of molecular weight of 26–30K was detected (FIG. 23A). The procedure gave 150 µg of BTC-I.

Figure 23B:
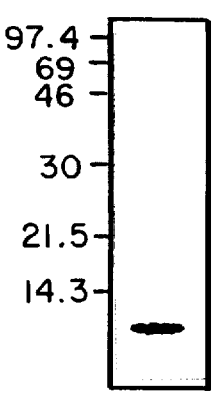
Figure 22B:
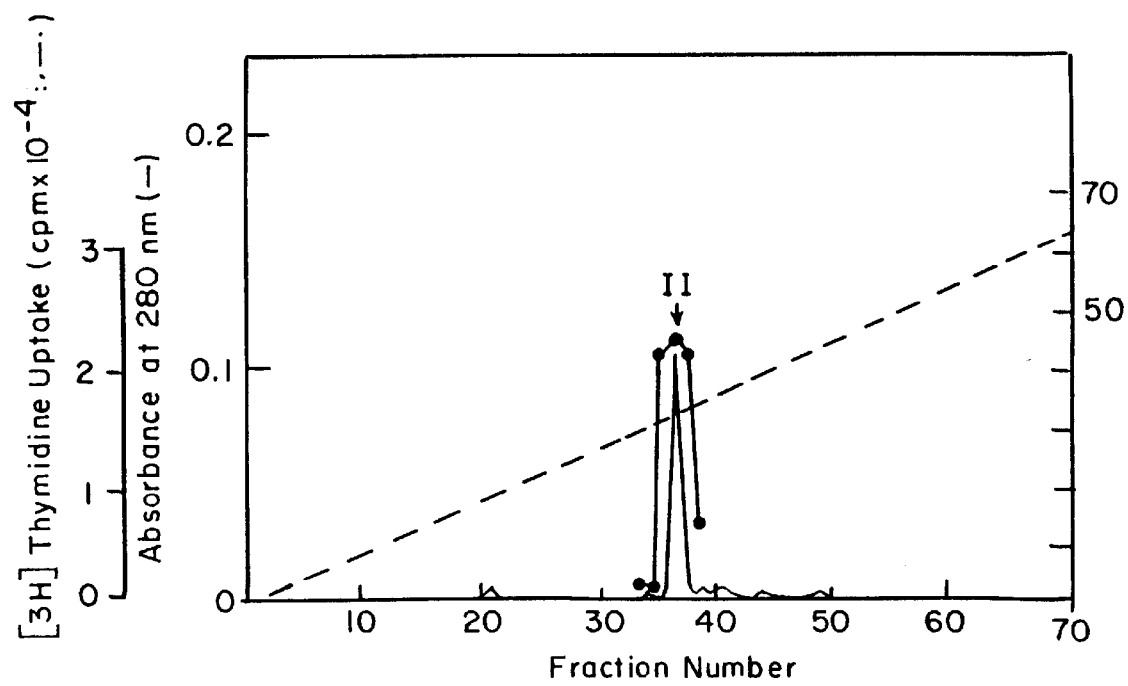

To the BTC-II fraction collected from the eluate of heparin column was added TFA to be a final concentration of 0.1%, and then the mixture was applied to C18 reverse phase HPLC column (Asahipak ODP50, diameter 0.46×15 cm, Asahi Chemical). The eluate thus obtained was applied to a gradient elution of acetonitrile (0–63%) in the presence of 0.1% TFA for 70 minutes and elutions were collected with each 0.5 ml (1 minute) (FIG. 22B). The biological activity was confirmed with the elution peak. From SDS-PAGE/ silver staining a single band below the position of molecular weight of 14K was detected (FIG. 23B). The procedure gave 75 μg of BTC-II.

EXAMPLE 13

(Purification of BTC-GF produced by a *E. coli* transformant.)

The transformant *E. coli* MM294 (DE3)/pLysS,pTB1516 was cultured for one night and the culture was transferred into a LB medium and the medium was cultivated at 37° C. for 2 hours. IPTG was added to the system to be final concentration of 0.1 mM and the cultivation was continued for 3 hours. The cells were collected by centrifugation and stored at −20° C.

Figure 24:
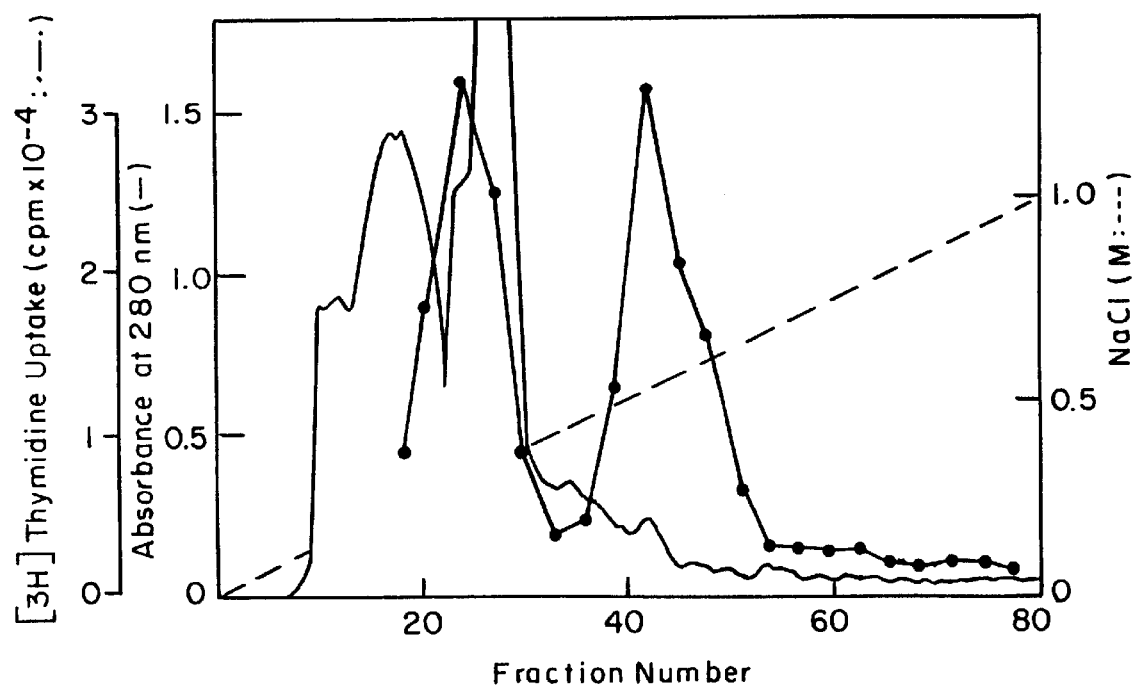
FIG. 24 shows the results of S-Sepharose column chromatography obtained in Example 13.

The stored cells corresponding to 5 liter culture were thawed and it was suspended in a 300 ml of buffer containing 50 mM Tris-HCl (pH 7.4), 10 mM EDTA, 0.2M NaCl, 10% sucrose and 1 mM APMSF (4-amidinophenyl)-methylsulfonyl fluoride). To the suspension 40 mg of egg white lysozyme was dissolved, and the solution was incubated at 4° C. for 2 hours and subjected to ultrasonic treatment and then centrifugation at 20000×g for 1 hour to give a supernatant. The supernatant was passed through 200 ml of Q-Sepharose bed, and TCA was added to the resultant to be a final concentration of 4% and stand still for 10 minutes at 4° C. A precipitate collected by centrifugation for 20 minutes at 20000×g was suspended to a buffer containing 100 ml of 20 mM-Tris(ph 7.4), 1 mM EDTA and 1 mM APMSF, and to the resultant 5N NaOH was added to adjust pH to 6, while homogenizing in a mortar. This homogenate was subjected to centrifugation at 100000×g for 1 hour, and the resulting supernatant was applied to S-Sepharose column (diameter 1.6×10 cm; Pharmacia). After washing a column with a buffer containing 0.1M potassium phosphate (pH6), 1 mM EDTA and 1 mM APMSF, a gradient elution was carried out with 400 ml of 0M to 1M of NaCl for 200 minutes. Each 5 ml of the eluates were collected. Highly active fractions Nos. 20 to 27 were pooled as *E. coli* BTC I (FIG. 24).

Figure 26:
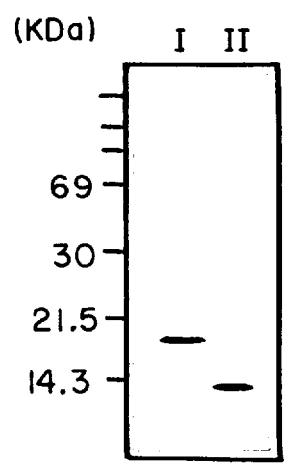
FIG. 26 shows the results of SDS-PAGE/silver staining obtained in Example 13.
Figure 25:
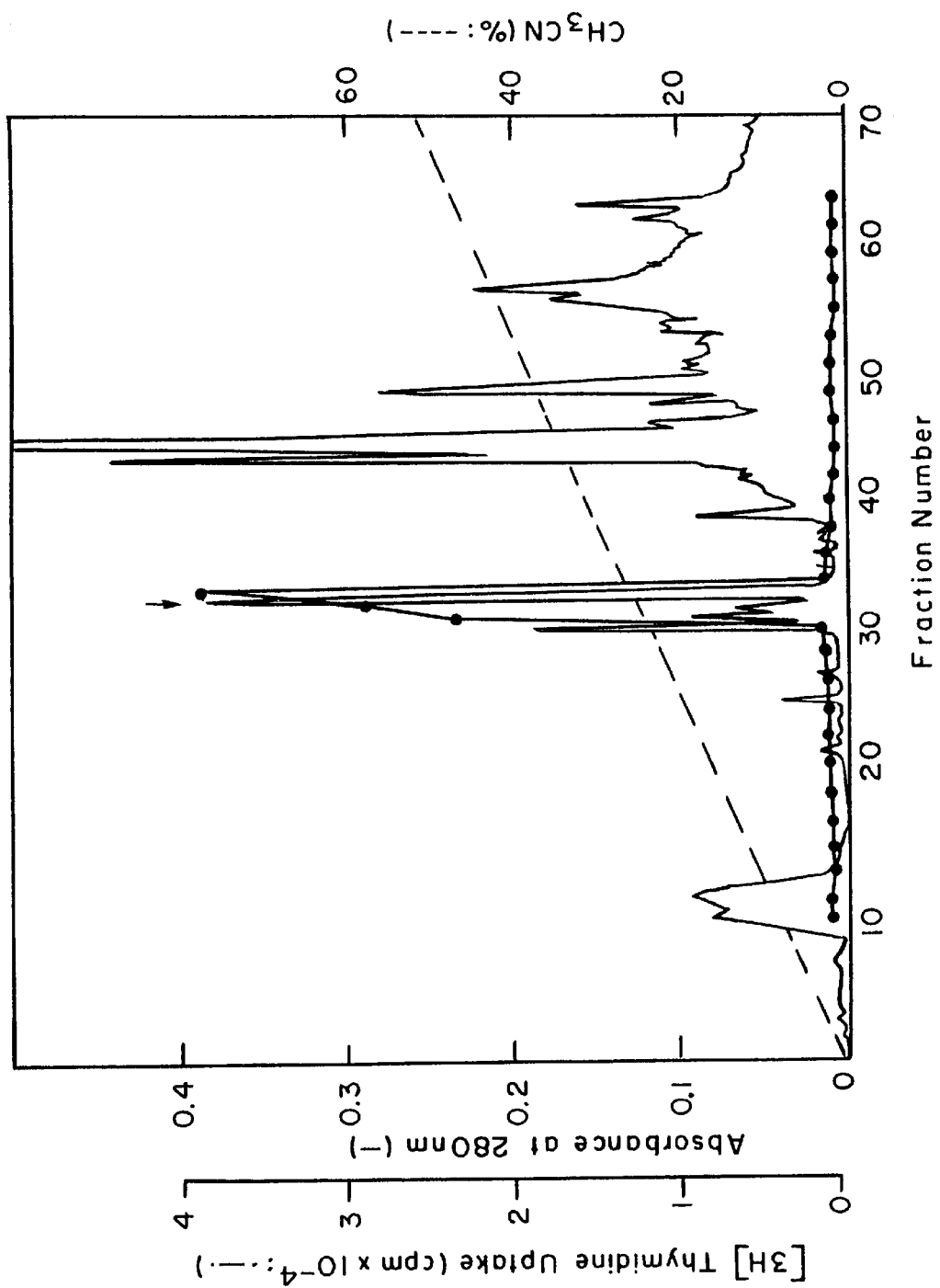
FIG. 25 shows the results of reverse-phase HPLC column chromatography obtained in Example 13.

To the pooled fraction TFA was added to be a final concentration of 0.1% and then the mixture was applied to C18 reverse phase HPLC column (Asahipak ODP-50, diameter 1.0×25 cm, Asahi Chemical). After washing the column with 0.1% TFA, the eluate thus obtained was applied to a gradient elution of 340 ml of acetonitrile (0–63%) for 170 minutes and elutions were collected with each 4 ml. The biological activity was confirmed with the elution peaks (FIG. 25). From SDS-PAGE/silver staining a band at the position of molecular weight of 18K was detected (FIG. 26, lane II). The procedure gave 630 μg of *E. coli* BTC-I.

Figures 27, 28:
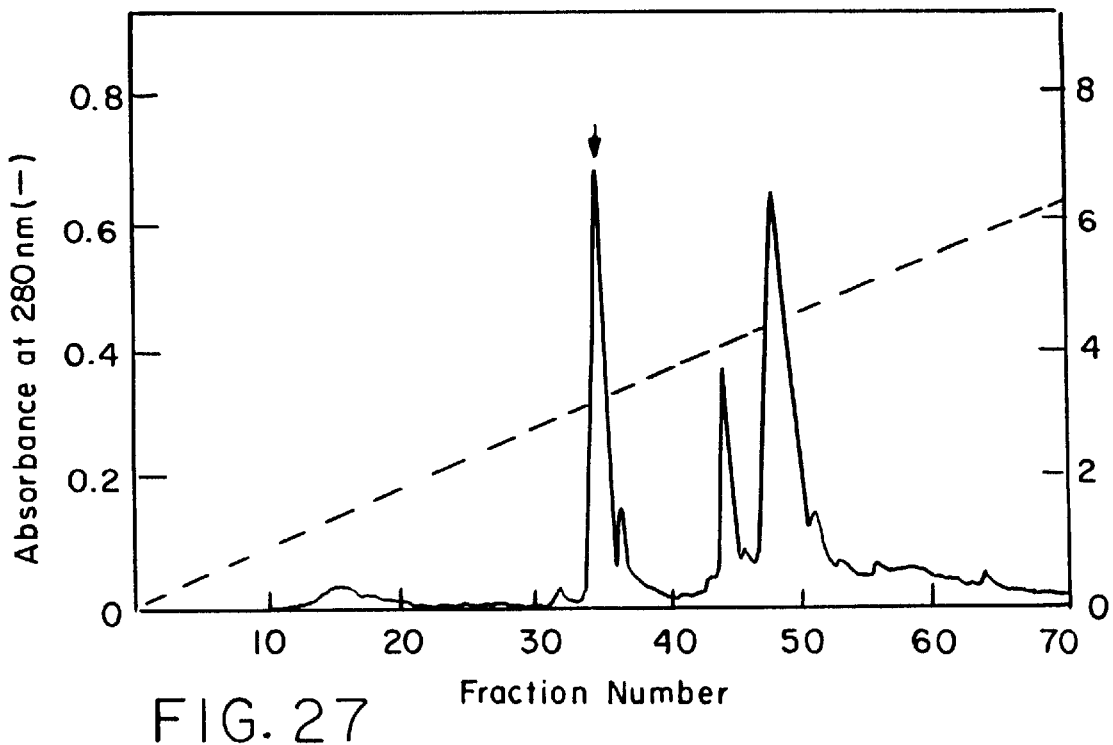
FIG. 27 shows the results of reverse-phase HPLC column chromatography obtained in Example 13.
FIG. 28 shows the amino acid sequences (SEQ ID NO:14, SEQ ID NO:15 and SEQ ID NO:16) in accordance with the results obtained in Example 13.

To the BTC-II fraction collected from the eluate of S-Sepharose was added TFA to a final concentration of 0.1%, and then the mixture was applied to C18 reverse phase HPLC column (Asahipak ODP-50, diameter 4.6×15 cm, Asahi Chemical). After washing the column with 0.1% TFA, the eluate thus obtained was applied to a gradient elution of 35 ml of acetonitrile (0–63%) for 70 minutes and elutions were collected with each 0.5 ml. The biological activity was confirmed with the elution peaks (FIG. 27). From SDS-PAGE/silver staining a band below the position of molecular weight of 14.3K (lysozyme) was detected (FIG. 26, lane II). The procedure gave 990 μg of *E. coli* BTC-II.

N-terminal amino acid sequence of *E. coli* BTC-I and BTC-II were determined up to 20 amino acids. The sequence of BTC-I was identical with that of the human BTC-GF, except Met derived from initiation codon, whereas BTC-II is a molecule which lacks 30 amino acids starting from Asp to Lys (see FIG. 28 (SEQ ID NO:14, SEQ ID NO:15, and SEQ ID NO:16)).

What is claimed:

1. A substantially pure recombinant non-glycosylated beta tumor cell growth factor, free from other protein of human origin, having amino acids No. 1 to 80 of SEQ. ID No. 18.

2. A peptide having the amino acids 2–15 of SEQ ID NO:3.

3. A peptide having the amino acids 17–23 of SEQ ID NO:3.

4. A peptide having the amino acids 25–30 of SEQ ID NO:3.

5. A peptide having the amino acids 38–48 of SEQ ID NO:3.

* * * * *